(12) United States Patent
Goble et al.

(10) Patent No.: US 6,780,180 B1
(45) Date of Patent: Aug. 24, 2004

(54) ELECTROSURGICAL INSTRUMENT

(75) Inventors: Nigel M Goble, Nr Cardiff (GB); Colin Co Goble, South Glamorgan (GB)

(73) Assignee: Gyrus Medical Limited, Cardiff (GB)

( * ) Notice: Subject to any disclaimer, the term of this patent is extended or adjusted under 35 U.S.C. 154(b) by 119 days.

(21) Appl. No.: 09/521,218

(22) Filed: Mar. 8, 2000

Related U.S. Application Data

(63) Continuation-in-part of application No. 09/318,615, filed on May 26, 1999, now Pat. No. 6,174,308, which is a division of application No. 08/737,302, filed as application No. PCT/GB96/01472 on Jun. 20, 1996, now Pat. No. 6,027,501, application No. 09/521,218, which is a continuation-in-part of application No. 09/198,396, filed on Nov. 24, 1998, now abandoned, which is a continuation of application No. 08/701,811, filed on Aug. 21, 1996, now Pat. No. 6,015,406.

(30) Foreign Application Priority Data

| Jun. 23, 1995 | (GB) | ............................................. 9512889 |
| Jan. 9, 1996 | (GB) | ............................................. 9600356 |
| Apr. 15, 1996 | (GB) | ............................................. 9600377 |
| Jun. 20, 1996 | (GB) | ............................................. 9612996 |

(51) Int. Cl.$^7$ .............................................. A61B 18/18
(52) U.S. Cl. ........................................ 606/41; 607/101
(58) Field of Search ............................ 606/41–52, 33, 606/34, 38, 27; 607/101, 102, 138; 128/DIG. 25

(56) References Cited

U.S. PATENT DOCUMENTS

| 164,184 A | 6/1875 | Kidder |
| 1,366,756 A | 1/1921 | Wappler |
| 1,735,271 A | 11/1929 | Groff |
| 1,814,791 A | 7/1931 | Ende |
| 1,889,609 A | 11/1932 | Mutscheller |
| 1,932,258 A | 10/1933 | Wappler |
| 1,943,543 A | 1/1934 | McFadden |
| 1,952,617 A | 3/1934 | Wappler |
| 1,983,669 A | 12/1934 | Kimble |
| 2,050,904 A | 8/1936 | Trice |

(List continued on next page.)

FOREIGN PATENT DOCUMENTS

| CH | 243478 | 7/1946 |
| DE | 651428 | 9/1937 |
| DE | 949370 | 3/1956 |
| DE | 1007960 | 5/1957 |
| DE | 2222820 | 11/1973 |

(List continued on next page.)

OTHER PUBLICATIONS

Benson et al. "Female Pelvic Floor Disorders" 1992, Norton Medical Books W.W. Norton & Company pp 239–240, 1992.*

(List continued on next page.)

Primary Examiner—Michael Peffley
(74) Attorney, Agent, or Firm—Nixon & Vanderhye P.C.

(57) ABSTRACT

An electrosurgical instrument, which is used for the treatment of tissue in the presence of an electrically-conductive fluid medium, comprises an instrument shaft (10), and an electrode assembly (12) at one end of the shaft. The electrode assembly (12) comprises a tissue treatment electrode (14) and a return electrode (18) which is electrically insulated from the tissue treatment electrode by means of an insulation member (16). The tissue treatment electrode (14) is exposed at the distal end portion of the instrument (10), and the return electrode (18) has a fluid contact surface spaced proximally from the exposed end of the tissue treatment electrode by the insulation member (16). The exposed end of the tissue treatment electrode (14) is constituted by a plurality of tissue treatment filamentary members made of an electrically-conductive material, the filamentary members being electrically connected to a common electrical supply conductor.

13 Claims, 9 Drawing Sheets

U.S. PATENT DOCUMENTS

| | | |
|---|---|---|
| 2,056,377 A | 10/1936 | Wappler |
| 2,196,191 A | 4/1940 | Arnesen |
| 2,888,928 A | 6/1959 | Seiger |
| 3,035,580 A | 5/1962 | Guiorguiev |
| 3,460,539 A | 8/1969 | Anhalt |
| 3,595,239 A | 7/1971 | Petersen |
| 3,601,126 A | 8/1971 | Estes |
| 3,614,414 A | 10/1971 | Gores |
| 3,648,001 A | 3/1972 | Anderson et al. |
| 3,685,518 A | 8/1972 | Beurle et al. |
| 3,699,967 A | 10/1972 | Anderson |
| 3,707,149 A | 12/1972 | Hao et al. |
| 3,801,766 A | 4/1974 | Morrison, Jr. |
| 3,815,604 A | 6/1974 | O'Malley et al. |
| 3,845,771 A | 11/1974 | Vise |
| 3,847,153 A | 11/1974 | Weissman |
| 3,870,047 A | 3/1975 | Gonser |
| 3,885,569 A | 5/1975 | Judson |
| 3,898,991 A | 8/1975 | Ikuno et al. |
| 3,901,242 A | 8/1975 | Storz |
| 3,902,494 A | 9/1975 | Haberlen et al. |
| 3,903,891 A | 9/1975 | Brayshaw |
| 3,920,021 A | 11/1975 | Hiltebrandt |
| 3,920,022 A | 11/1975 | Pastor |
| 3,923,063 A | 12/1975 | Andrews et al. |
| 3,929,137 A | 12/1975 | Gonser et al. |
| 3,939,839 A | 2/1976 | Curtiss |
| 3,945,375 A | 3/1976 | Banko |
| 3,963,030 A | 6/1976 | Newton |
| 3,964,487 A | 6/1976 | Judson |
| 3,970,088 A | 7/1976 | Morrison |
| 3,974,833 A | 8/1976 | Durden, III |
| 4,011,872 A | 3/1977 | Komiya |
| 4,016,881 A | 4/1977 | Rioux et al. |
| 4,024,467 A | 5/1977 | Andrews et al. |
| 4,033,351 A | 7/1977 | Hetzel |
| 4,040,426 A | 8/1977 | Morrison, Jr. |
| 4,043,342 A | 8/1977 | Morrison, Jr. |
| 4,051,855 A | 10/1977 | Schneiderman |
| 4,060,088 A | 11/1977 | Morrison, Jr. et al. |
| 4,069,827 A | 1/1978 | Dominy |
| 4,074,718 A | 2/1978 | Morrison, Jr. |
| 4,092,986 A | 6/1978 | Schneiderman |
| 4,114,623 A | 9/1978 | Meinke et al. |
| 4,116,198 A | 9/1978 | Roos |
| 4,119,102 A | 10/1978 | LeVeen |
| 4,126,137 A | 11/1978 | Archibald |
| 4,154,240 A | 5/1979 | Ikuno et al. |
| 4,189,685 A | 2/1980 | Doss |
| 4,200,104 A | 4/1980 | Harris |
| 4,202,337 A | 5/1980 | Hren et al. |
| 4,204,549 A | 5/1980 | Paglione |
| 4,210,152 A | 7/1980 | Berry |
| 4,228,800 A | 10/1980 | Degler, Jr. et al. |
| 4,248,231 A | 2/1981 | Herczog et al. |
| 4,271,837 A | 6/1981 | Schuler |
| 4,281,373 A | 7/1981 | Mabille |
| 4,301,802 A | 11/1981 | Poler |
| 4,326,529 A | 4/1982 | Doss et al. |
| 4,346,332 A | 8/1982 | Walden |
| 4,376,263 A | 3/1983 | Pittroff et al. |
| 4,381,007 A | 4/1983 | Doss |
| 4,416,277 A | 11/1983 | Newton et al. |
| 4,418,692 A | 12/1983 | Guay |
| 4,429,698 A | 2/1984 | Bentall |
| 4,448,198 A | 5/1984 | Turner |
| 4,474,179 A | 10/1984 | Koch |
| 4,476,862 A | 10/1984 | Pao |
| 4,492,231 A | 1/1985 | Auth |
| 4,494,541 A | 1/1985 | Archibald |
| 4,512,338 A | 4/1985 | Balko et al. |
| 4,517,976 A | 5/1985 | Murakoshi et al. |
| 4,524,770 A | 6/1985 | Orandi |
| 4,532,924 A | 8/1985 | Auth et al. |
| 4,534,347 A | 8/1985 | Taylor |
| 4,548,207 A | 10/1985 | Reimels |
| 4,559,943 A | 12/1985 | Bowers |
| 4,559,951 A | 12/1985 | Dahl et al. |
| 4,562,838 A | 1/1986 | Walker |
| 4,565,200 A | 1/1986 | Cosman |
| 4,567,890 A | 2/1986 | Ohta et al. |
| 4,580,557 A | 4/1986 | Hertzmann |
| 4,590,934 A | 5/1986 | Malis et al. |
| 4,593,691 A | 6/1986 | Lindstrom et al. |
| 4,617,927 A | 10/1986 | Manes |
| 4,657,015 A | 4/1987 | Irnich |
| 4,658,819 A | 4/1987 | Harris et al. |
| 4,658,820 A | 4/1987 | Klicek |
| 4,669,468 A | 6/1987 | Cartmell et al. |
| 4,674,499 A | 6/1987 | Pao |
| 4,681,122 A | 7/1987 | Winters et al. |
| 4,682,596 A | 7/1987 | Bales et al. |
| 4,688,569 A | 8/1987 | Rabinowitz |
| 4,696,668 A | 9/1987 | Wilcox |
| 4,706,667 A | 11/1987 | Roos |
| 4,709,698 A | 12/1987 | Johnston et al. |
| 4,712,544 A | 12/1987 | Ensslin |
| 4,727,874 A | 3/1988 | Bowers et al. |
| 4,735,201 A | 4/1988 | O'Reilly |
| 4,739,759 A | 4/1988 | Rexroth et al. |
| 4,769,005 A | 9/1988 | Ginsburg et al. |
| 4,781,175 A | 11/1988 | McGreevy et al. |
| 4,799,480 A | 1/1989 | Abraham et al. |
| 4,800,899 A | 1/1989 | Elliott |
| 4,802,476 A | 2/1989 | Noerenberg et al. |
| 4,805,616 A | 2/1989 | Pao |
| 4,813,429 A | 3/1989 | Eshel et al. |
| 4,820,298 A | 4/1989 | Leveen et al. |
| 4,823,791 A | 4/1989 | D'Amelio et al. |
| 4,827,927 A | 5/1989 | Newton |
| 4,832,048 A | 5/1989 | Cohen |
| 4,850,353 A | 7/1989 | Stasz et al. |
| 4,860,744 A | 8/1989 | Johnson et al. |
| 4,878,493 A | 11/1989 | Pasternak et al. |
| 4,886,074 A | 12/1989 | Bisping |
| 4,919,129 A | 4/1990 | Weber, Jr. et al. |
| 4,920,978 A | 5/1990 | Colvin |
| 4,931,047 A | 6/1990 | Broadwin et al. |
| 4,936,281 A | 6/1990 | Stasz |
| 4,936,301 A | 6/1990 | Rexroth et al. |
| 4,936,310 A | 6/1990 | Engstrom et al. |
| 4,936,842 A | 6/1990 | D'Amelio et al. |
| 4,943,290 A | 7/1990 | Rexroth et al. |
| 4,950,267 A | 8/1990 | Ishihara et al. |
| 4,955,377 A | 9/1990 | Lennox et al. |
| 4,966,597 A | 10/1990 | Cosman |
| 4,967,765 A | 11/1990 | Turner et al. |
| 4,969,885 A | 11/1990 | Farin |
| 4,976,711 A | 12/1990 | Parins et al. |
| 4,994,069 A | 2/1991 | Ritchart et al. |
| 4,998,933 A | 3/1991 | Eggers et al. |
| 5,007,908 A | 4/1991 | Rydell |
| 5,009,656 A | 4/1991 | Reimels |
| 5,013,312 A | 5/1991 | Parins et al. |
| 5,019,076 A | 5/1991 | Yamanashi et al. |
| 5,035,696 A | 7/1991 | Rydell |
| 5,037,379 A | 8/1991 | Clayman et al. |
| 5,047,026 A | 9/1991 | Rydell |
| 5,047,027 A | 9/1991 | Rydell |
| 5,057,107 A | 10/1991 | Parins et al. |
| 5,062,031 A | 10/1991 | Flachenecker et al. |

| Patent | Date | Inventor |
|---|---|---|
| 5,071,418 A | 12/1991 | Rosenbaum |
| 5,080,660 A | 1/1992 | Buelna |
| 5,083,565 A | 1/1992 | Parins |
| 5,085,659 A | 2/1992 | Rydell |
| 5,088,997 A | 2/1992 | Delahuerga et al. |
| 5,098,431 A | 3/1992 | Rydell |
| 5,099,840 A | 3/1992 | Goble et al. |
| 5,108,391 A | 4/1992 | Flachenecker et al. |
| 5,108,407 A | 4/1992 | Geremia et al. |
| RE33,925 E | 5/1992 | Bales et al. |
| 5,117,978 A | 6/1992 | Blumenfeld et al. |
| 5,122,138 A | 6/1992 | Manwaring |
| 5,133,365 A | 7/1992 | Heil, Jr. et al. |
| 5,158,561 A | 10/1992 | Rydell et al. |
| 5,167,658 A | 12/1992 | Ensslin |
| 5,167,659 A | 12/1992 | Ohtomo et al. |
| 5,171,255 A | 12/1992 | Rydell |
| 5,171,311 A | 12/1992 | Rydell et al. |
| 5,178,620 A | 1/1993 | Eggers et al. |
| 5,190,517 A | 3/1993 | Zieve et al. |
| 5,195,959 A | 3/1993 | Smith |
| 5,196,007 A | 3/1993 | Ellman et al. |
| 5,197,963 A | 3/1993 | Parins |
| 5,201,743 A | 4/1993 | Haber et al. |
| 5,207,675 A | 5/1993 | Canady |
| 5,211,625 A | 5/1993 | Sakurai et al. |
| 5,217,457 A | 6/1993 | Delahuerga et al. |
| 5,217,458 A | 6/1993 | Parins |
| 5,217,459 A | 6/1993 | Kamerling |
| 5,221,281 A | 6/1993 | Klicek |
| 5,244,462 A | 9/1993 | Delahuerga et al. |
| 5,249,585 A | 10/1993 | Turner et al. |
| 5,250,047 A | 10/1993 | Rydell |
| 5,257,990 A | 11/1993 | Nash |
| 5,258,006 A | 11/1993 | Rydell et al. |
| 5,259,395 A | 11/1993 | Li |
| 5,261,906 A | 11/1993 | Pennino et al. |
| 5,267,994 A | 12/1993 | Gentelia et al. |
| 5,267,997 A | 12/1993 | Farin et al. |
| 5,277,201 A | 1/1994 | Stern |
| 5,277,696 A | 1/1994 | Hagen |
| 5,281,213 A | 1/1994 | Milder et al. |
| 5,281,216 A | 1/1994 | Klicek |
| 5,282,799 A | 2/1994 | Rydell |
| 5,282,845 A | 2/1994 | Bush et al. |
| 5,290,282 A | 3/1994 | Casscells |
| 5,290,283 A | 3/1994 | Suda |
| 5,300,068 A | 4/1994 | Rosar et al. |
| 5,300,069 A | 4/1994 | Hunsberger et al. |
| 5,300,070 A | 4/1994 | Gentelia et al. |
| 5,304,169 A * | 4/1994 | Sand .............................. 606/5 |
| 5,304,214 A | 4/1994 | DeFord et al. |
| 5,306,238 A | 4/1994 | Fleenor |
| 5,317,155 A | 5/1994 | King |
| 5,318,563 A | 6/1994 | Malis et al. |
| 5,320,627 A | 6/1994 | Sorensen et al. |
| 5,330,470 A | 7/1994 | Hagen |
| 5,330,471 A | 7/1994 | Eggers |
| 5,334,193 A | 8/1994 | Nardella |
| 5,334,198 A | 8/1994 | Hart et al. |
| 5,336,222 A | 8/1994 | Durgin, Jr. et al. |
| 5,342,357 A | 8/1994 | Nardella |
| 5,342,391 A | 8/1994 | Foshee et al. |
| 5,344,428 A | 9/1994 | Griffiths |
| 5,352,222 A | 10/1994 | Rydell |
| 5,354,296 A | 10/1994 | Turkel |
| 5,366,443 A | 11/1994 | Eggers et al. |
| 5,370,645 A | 12/1994 | Klicek et al. |
| 5,370,671 A * | 12/1994 | Maurer et al. .............. 607/138 |
| 5,370,675 A | 12/1994 | Edwards et al. |
| 5,372,596 A | 12/1994 | Klicek et al. |
| 5,374,265 A * | 12/1994 | Sand .............................. 606/5 |
| 5,382,247 A | 1/1995 | Cimino et al. |
| 5,383,874 A | 1/1995 | Jackson et al. |
| 5,383,876 A | 1/1995 | Nardella |
| 5,383,917 A | 1/1995 | Desai et al. |
| 5,383,923 A | 1/1995 | Webster, Jr. |
| 5,395,363 A | 3/1995 | Billings et al. |
| 5,395,368 A | 3/1995 | Ellman et al. |
| 5,403,311 A | 4/1995 | Abele et al. |
| 5,419,767 A | 5/1995 | Eggers et al. |
| 5,422,567 A | 6/1995 | Matsunaga |
| 5,423,808 A | 6/1995 | Edwards et al. |
| 5,423,809 A | 6/1995 | Klicek |
| 5,423,810 A | 6/1995 | Goble et al. |
| 5,423,811 A | 6/1995 | Imran et al. |
| 5,431,649 A | 7/1995 | Mulier et al. |
| 5,437,662 A | 8/1995 | Nardella |
| 5,438,302 A | 8/1995 | Goble |
| 5,441,499 A | 8/1995 | Fritzsch |
| 5,443,470 A | 8/1995 | Stern et al. |
| 5,451,223 A | 9/1995 | Ben-Simhon |
| 5,454,809 A | 10/1995 | Janssen |
| 5,458,596 A * | 10/1995 | Lax et al. .................... 606/31 |
| 5,462,521 A | 10/1995 | Brucker et al. |
| 5,472,441 A | 12/1995 | Edwards et al. |
| 5,472,443 A | 12/1995 | Cordis et al. |
| 5,480,397 A | 1/1996 | Eggers et al. |
| 5,480,398 A | 1/1996 | Eggers |
| 5,496,312 A | 3/1996 | Klicek |
| 5,496,314 A | 3/1996 | Eggers |
| 5,505,728 A | 4/1996 | Ellman et al. |
| 5,505,730 A | 4/1996 | Edwards |
| 5,507,743 A | 4/1996 | Edwards et al. |
| 5,509,916 A | 4/1996 | Taylor |
| 5,514,129 A | 5/1996 | Smith |
| 5,514,130 A * | 5/1996 | Baker ......................... 606/41 |
| 5,514,131 A | 5/1996 | Edwards et al. |
| 5,520,684 A | 5/1996 | Imran |
| 5,520,685 A | 5/1996 | Wojciechowicz |
| 5,522,815 A | 6/1996 | Durgin, Jr. et al. |
| 5,527,331 A | 6/1996 | Kresch et al. |
| 5,531,744 A | 7/1996 | Nardella et al. |
| 5,536,267 A | 7/1996 | Edwards et al. |
| 5,540,680 A | 7/1996 | Guglielmi et al. |
| 5,540,681 A | 7/1996 | Strul et al. |
| 5,540,682 A | 7/1996 | Gardner et al. |
| 5,540,683 A | 7/1996 | Ichikawa et al. |
| 5,540,684 A | 7/1996 | Hassler, Jr. |
| 5,540,685 A | 7/1996 | Parins et al. |
| 5,542,916 A | 8/1996 | Hirsch et al. |
| 5,542,945 A | 8/1996 | Fritzsch |
| 5,545,161 A | 8/1996 | Imran |
| 5,545,193 A | 8/1996 | Fleischman et al. |
| 5,549,605 A | 8/1996 | Hahnen |
| 5,554,172 A | 9/1996 | Horner et al. |
| 5,555,618 A | 9/1996 | Winkler |
| 5,556,396 A * | 9/1996 | Cohen et al. ................ 606/42 |
| 5,556,397 A | 9/1996 | Long et al. |
| 5,558,671 A | 9/1996 | Yates |
| 5,562,720 A | 10/1996 | Stern et al. |
| 5,569,164 A | 10/1996 | Lurz |
| 5,569,242 A * | 10/1996 | Lax et al. .................... 606/42 |
| 5,569,244 A | 10/1996 | Hahnen |
| 5,569,245 A | 10/1996 | Guglielmi et al. |
| 5,575,789 A | 11/1996 | Bell et al. |
| 5,578,007 A | 11/1996 | Imran |
| 5,582,609 A | 12/1996 | Swanson et al. |
| 5,582,610 A | 12/1996 | Grossi et al. |
| 5,584,830 A | 12/1996 | Ladd et al. |
| 5,588,960 A * | 12/1996 | Edwards et al. .............. 606/48 |
| 5,591,141 A | 1/1997 | Nettekoven |

| | | | | | | |
|---|---|---|---|---|---|---|
| 5,599,344 | A | 2/1997 | Paterson | DE | 3622337 C2 | 1/1988 |
| 5,599,345 | A | 2/1997 | Edwards et al. | DE | 3642077 C2 | 6/1988 |
| 5,599,346 | A | 2/1997 | Edwards et al. | DE | 3708801 C2 | 9/1988 |
| 5,599,347 | A | 2/1997 | Hart et al. | DE | 3824913 | 2/1990 |
| 5,599,348 | A | 2/1997 | Gentelia et al. | DE | 3838840 C2 | 5/1990 |
| 5,599,349 | A | 2/1997 | D'Amelio | DE | 3930451 | 3/1991 |
| 5,603,711 | A | 2/1997 | Parins et al. | DE | 4108269 C2 | 6/1992 |
| 5,603,712 | A | 2/1997 | Koranda et al. | DE | 4103972 C2 | 8/1992 |
| 5,607,422 | A | 3/1997 | Smeets et al. | DE | 4126608 | 2/1993 |
| 5,609,151 | A | 3/1997 | Mulier et al. | DE | 4139029 C2 | 6/1993 |
| 5,609,573 | A | 3/1997 | Sandock | DE | 4217999 A1 | 12/1993 |
| 5,609,598 | A * | 3/1997 | Laufer et al. ............... 606/142 | DE | 4237321 A1 | 5/1994 |
| 5,611,798 | A | 3/1997 | Eggers | DE | 4323585 | 1/1995 |
| 5,620,481 | A | 4/1997 | Desai et al. | DE | 4339049 | 5/1995 |
| 5,624,439 | A | 4/1997 | Edwards et al. | DE | 4425015 | 1/1996 |
| 5,626,560 | A | 5/1997 | Soring | DE | 4429478 | 3/1996 |
| 5,626,575 | A | 5/1997 | Crenner | DE | 19530004 A | 3/1996 |
| 5,626,576 | A | 5/1997 | Janssen | DE | 19510185 A | 10/1996 |
| 5,626,578 | A | 5/1997 | Tihon | DE | 19512640 C2 | 10/1996 |
| 5,628,745 | A | 5/1997 | Bek | DE | 19514553 C1 | 10/1996 |
| 5,628,771 | A | 5/1997 | Mizukawa et al. | EP | 0 013605 | 7/1980 |
| 5,630,426 | A | 5/1997 | Eggers et al. | EP | 0 049633 | 4/1982 |
| 5,633,578 | A | 5/1997 | Eggers et al. | EP | 0 067680 | 12/1982 |
| 5,634,924 | A | 6/1997 | Turkel et al. | EP | 0 136855 | 4/1985 |
| 5,669,907 | A | 9/1997 | Platt, Jr. et al. | EP | 0 219568 | 12/1985 |
| 5,672,174 | A | 9/1997 | Gough et al. | EP | 0 205851 | 12/1986 |
| 5,683,366 | A | 11/1997 | Eggers et al. | EP | 0 280798 A | 9/1988 |
| 5,693,045 | A | 12/1997 | Eggers | EP | 0 310431 | 4/1989 |
| 5,697,281 | A | 12/1997 | Eggers et al. | EP | 0 316469 | 5/1989 |
| 5,697,536 | A | 12/1997 | Eggers et al. | EP | 0 325456 | 7/1989 |
| 5,697,882 | A | 12/1997 | Eggers et al. | EP | 0 332308 | 9/1989 |
| 5,697,909 | A | 12/1997 | Eggers et al. | EP | 0 373670 | 6/1990 |
| 5,700,262 | A | 12/1997 | Acosta et al. | EP | 0 392837 | 10/1990 |
| 5,725,524 | A | 3/1998 | Mulier et al. | EP | 0 407057 | 1/1991 |
| 5,735,846 | A | 4/1998 | Panescu et al. | EP | 0 412426 | 2/1991 |
| 5,749,869 | A | 5/1998 | Lindenmeier et al. | EP | 0 437377 | 7/1991 |
| 5,755,753 | A * | 5/1998 | Knowlton .................... 607/98 | EP | 0 448798 | 10/1991 |
| 5,766,153 | A | 6/1998 | Eggers et al. | EP | 0 499491 | 8/1992 |
| 5,776,092 | A | 7/1998 | Farin et al. | EP | 0 507622 | 10/1992 |
| 5,810,764 | A | 9/1998 | Eggers et al. | EP | 0 509670 | 10/1992 |
| 5,833,689 | A | 11/1998 | Long | EP | 0 517243 | 12/1992 |
| 5,843,019 | A | 12/1998 | Eggers et al. | EP | 0 518230 | 12/1992 |
| 5,860,951 | A | 1/1999 | Eggers et al. | EP | 0 530400 | 3/1993 |
| 5,868,739 | A | 2/1999 | Lindenmeier et al. | EP | 0 536440 | 4/1993 |
| 5,871,469 | A | 2/1999 | Eggers et al. | EP | 0 558316 | 9/1993 |
| 5,873,855 | A | 2/1999 | Eggers et al. | EP | 0 558318 | 9/1993 |
| 5,888,198 | A | 3/1999 | Eggers et al. | EP | 0 647435 | 4/1995 |
| 5,891,095 | A | 4/1999 | Eggers et al. | EP | 0 653192 | 5/1995 |
| 5,902,272 | A | 5/1999 | Eggers et al. | EP | 0 667680 | 8/1995 |
| 5,919,191 | A | 7/1999 | Lennox et al. | EP | 0 674909 | 10/1995 |
| 5,941,876 | A | 8/1999 | Nardella et al. | EP | 0 684015 | 11/1995 |
| 6,004,319 | A | 12/1999 | Goble et al. | EP | 0 688536 | 12/1995 |
| 6,022,347 | A | 2/2000 | Lindenmeier et al. | EP | 0 692224 | 1/1996 |
| 6,073,052 | A * | 6/2000 | Zelickson et al. .......... 607/100 | EP | 0 694290 | 1/1996 |
| 6,091,995 | A | 7/2000 | Ingle et al. | EP | 0 697199 | 2/1996 |
| 6,241,753 | B1 * | 6/2001 | Knowlton .................... 607/99 | EP | 0 709065 | 5/1996 |
| | | | | EP | 0 714635 | 6/1996 |
| | | FOREIGN PATENT DOCUMENTS | | EP | 0 717967 | 6/1996 |
| DE | | 2457900 | 5/1976 | EP | 0 732080 | 9/1996 |
| DE | | 2930982 | 2/1981 | EP | 0 733345 | 9/1996 |
| DE | | 3209444 | 10/1982 | EP | 0 737447 | 10/1996 |
| DE | | 3215832 A | 11/1982 | EP | 0 754437 | 1/1997 |
| DE | | 3119735 | 1/1983 | FR | 57862 | 9/1953 |
| DE | | 3245570 | 6/1984 | FR | 1215305 | 4/1960 |
| DE | | 222207 | 5/1985 | FR | 1454773 | 10/1966 |
| DE | | 3423356 | 1/1986 | FR | 2313949 | 1/1977 |
| DE | | 3427517 | 1/1986 | FR | 2443829 | 7/1980 |
| DE | | 3511107 | 10/1986 | FR | 2501034 | 9/1982 |
| DE | | 3623688 | 1/1987 | FR | 2645008 | 10/1990 |
| DE | | 3530335 | 3/1987 | GB | 1361497 | 7/1974 |
| DE | | 3707820 | 9/1987 | GB | 2037167 | 7/1980 |

| | | |
|---|---|---|
| GB | 1583397 | 1/1981 |
| GB | 2084880 | 4/1982 |
| GB | 2101893 | 1/1983 |
| GB | 2133290 | 7/1984 |
| GB | 2145932 | 4/1985 |
| GB | 2161081 | 1/1986 |
| GB | 2164473 | 3/1986 |
| GB | 2165761 | 4/1986 |
| GB | 2177309 | 1/1987 |
| GB | 2179861 | 3/1987 |
| GB | 2213381 | 8/1989 |
| GB | 2214430 | 9/1989 |
| GB | 2269538 | 2/1994 |
| GB | PCT/GB97/00066 | 5/1997 |
| JP | 62211060 | 9/1987 |
| RU | 644491 | 1/1979 |
| WO | WO 81/03271 | 11/1981 |
| WO | WO 82/00084 | 1/1982 |
| WO | WO 82/02488 | 8/1982 |
| WO | WO 84/03829 | 10/1984 |
| WO | WO 88/01851 | 3/1988 |
| WO | WO 90/03152 | 4/1990 |
| WO | WO 93/08756 | 5/1993 |
| WO | WO 93/13718 | 7/1993 |
| WO | WO 93/13816 | 7/1993 |
| WO | WO 93/16650 | 9/1993 |
| WO | WO 93/19681 | 10/1993 |
| WO | WO 93/19682 | 10/1993 |
| WO | WO 93/20747 | 10/1993 |
| WO | WO 93/20877 | 10/1993 |
| WO | WO 94/04220 | 3/1994 |
| WO | WO 94/06510 | 3/1994 |
| WO | WO 94/10921 | 5/1994 |
| WO | WO 94/10924 | 5/1994 |
| WO | WO 94/10925 | 5/1994 |
| WO | WO 94/23659 | 10/1994 |
| WO | WO 94/26228 | 11/1994 |
| WO | WO 94/28809 | 12/1994 |
| WO | WO 95/02369 | 1/1995 |
| WO | WO 95/05781 | 3/1995 |
| WO | WO 95/09576 | 4/1995 |
| WO | WO 95/09577 | 4/1995 |
| WO | WO 95/10320 | 4/1995 |
| WO | WO 95/10321 | 4/1995 |
| WO | WO 95/17855 | 7/1995 |
| WO | WO 95/18575 | 7/1995 |
| WO | WO 95/19733 | 7/1995 |
| WO | WO 95/20360 | 8/1995 |
| WO | WO 95/23558 | 9/1995 |
| WO | WO 95/24160 | 9/1995 |
| WO | WO 95/25472 | 9/1995 |
| WO | WO 95/26686 | 10/1995 |
| WO | WO 95/30377 | 11/1995 |
| WO | WO 95/31144 | 11/1995 |
| WO | WO 96/00036 | 1/1996 |
| WO | WO 96/00039 | 1/1996 |
| WO | WO 96/00040 | 1/1996 |
| WO | WO 96/00042 | 1/1996 |
| WO | WO 96/00043 | 1/1996 |
| WO | WO 96/00528 | 1/1996 |
| WO | WO 96/04859 | 2/1996 |
| WO | WO 96/07360 | 3/1996 |
| WO | WO 96/09010 | 3/1996 |
| WO | WO 96/10367 | 4/1996 |
| WO | WO 96/11638 | 4/1996 |
| WO | WO 96/14020 | 5/1996 |
| WO | WO 96/14021 | 5/1996 |
| WO | WO 96/18349 | 6/1996 |
| WO | WO 96/19152 | 6/1996 |
| WO | WO 96/23448 | 8/1996 |
| WO | WO 96/23449 | 8/1996 |
| WO | WO 96/24296 | 8/1996 |
| WO | WO 96/24301 | 8/1996 |
| WO | WO 96/27337 | 9/1996 |
| WO | WO 96/29946 | 10/1996 |

OTHER PUBLICATIONS

Raz et al, "Female Urology" 2nd Ed, W.B. Saunders Company Chapter 30 pp 344–357.*

Cook, Albert M. & John G. Webster, *Therapeutic Medical Devices Application and Design*, Prentice–Hall Inc., New Jersey, 1982, p. 349.

Pearce, John A., *Electrosurgery*, John Wiley & Sons Inc., New York, 1986, pp. 17, 69–75 and 87.

Wyeth, G.A., *Electrosurgical Unit*, pp. 1180–1202.

Everest Medical Technologies, Inc., "Everest Bipolar Laparoscopic Cholecytectomy," Transcript of Lecture by Dr. Olsen, Oct. 7, 1991.

Dobbie, A.K., "The Electrical Aspects of Surgical Diathermy," Biomedical Engineering, May 1969, pp. 206–216.

Valleylab, Excerpts from Valleylab SSE2L Instruction Manual, Valleylab Part No. A 945 110 005 H, Jan. 6, 1983.

Schurr, M. O. et al., "Histologic Effects of Different Technologies of Dissection in Endoscopic Surgery:Nd:YAG Laser, High Frequency and Water–Jet," End. Surg., vol. 2, 1994, pp. 195–201.

Newman, Laura, "Could Twist on TURP Knock Lasers Out," Urology Times, vol. 3, No. 3, Mar. 1995, p. 21.

ArthroCare Corporation, "The Arthrocare Arthroscopic System," 1995.

Tucker, R.D. et al., In Vivo Effect of 5 French Bipolar and Monopolar Electro–Surgical Probes on Porcine Bladder, Urological Research, Springer–Verlag 1990, 18:291–294.

Kramolowsky, Eugene V. et al., "The Urological Application of Electrosurgery," The Journal of Urology, vol. 146, Sep. 1991, pp. 669–674.

Tucker, Robert D. et al., "A Comparison of Urologic Application of Bipolar Versus Monopolar Five French Electrosurgical Probes," The Journal of Urology, vol. 141, Mar. 1989, pp. 662–665.

Kramolowsky, Eugene V. et al., "Use of 5F Bipolar Electrosurgical Probe in Endoscopic Urological Procedures," The Journal of Urology, vol. 143, Feb. 1990, pp. 275–277.

Tucker, Robert et al., A Bipolar Electrosurgical TURP Loop, Abstract of Paper P14–11, 7th World Congress on Endourology and ESWL, Nov. 27–30, Kyoto, Japan, 1989, p. 248.

Ramsay, J.W. A. et al., "A Comparison of Bipolar and Monopolar Diathermy Probes in Experimental Animals," Urological Research, Springer–Verlag 1985, 13:99–102.

German Article w/ Translation: Elsasser, E. and Roos, E., "Concerning an Instrument for Transurethal Resection without Leakage of Current," Medizinal–Marks/Acta Medicotechnica, vol. 24, No. 4, 1976, pp. 129–134.

Nardella, Paul C., "Radio Frequency Energy and Impedance Feedback," SPIE, vol. 1068, Catheter–Based Sensing & Imaging Technology, 1989, pp. 42–48.

Honig, WIlliam M., "The Mechanism of Cutting in Electrosurgery," IEEE Transactions on Biomedical Engineering, Jan. 1975, pp. 58–65.

Barry, Kevin J. et al. "The Effect of Radiofrequency–Generated Thermal Energy on the Mechanical and Histologic Characteristics of the Arterial Wall in Vivo: Implications for Radiofrequency Angioplasty," American Heart Journal, vol. 117, No. 2, Feb. 1989, pp. 332–341.

Slager, Cornelis J. et al., "Vaporization of Atherosclerotic Plaques by Spark Erosion," Journal of American College of Cardiology, 1985, pp. 1382–1386.

Lee, Benjamin I. et al., "Thermal Compression and Molding of Atherosclerotic Vascular Tissue with Use of Radiofrequency Energy: Implications for Radiofrequency Balloon Angioplasty," Journal of American College of Cardiology, vol. 13, No. 5, Apr. 1989, pp. 1167–1175.

Piercey, J.R.A. et al., "Electrosurgical Treatment of Experimental Bleeding Canine Gastric Ulcers," Gastroenterology, vol. 74, No. 3, 1978, pp. 527–534.

Protell, Robert L. et al., "Computer–Assisted Electrocoagulation: Bipolar vs. Monopolar in the Treatment of Experimental Canine Gastric Ulcer Bleeding," Gastroenterology, vol. 80, No. 3, 1981, pp. 451–455.

Johnston, James H. et al., "Experimental Comparison of Endoscopic Yttrium–Aluminum–Garnet Laser, Electrosurgery, and Heater Probe for Canine Gut Arterial Coagulation," Gastroenterology, vol. 92, No. 5, May. 1987, pp. 1101–1108.

Dennis, M.B. et al., "Evaluation of Electrofulguration in Control of Bleeding of Experimental Gastric Ulcers," Digestive Diseases and Sciences, vol. 24, No. 11, Nov. 1979, pp. 845–848.

Silverstein, Fred E. et al., "Endoscopic Hemostasis Using Laser Photocoagulation and Electrocoagulation," Digestive Diseases and Sciences, vol. 26, No. 7, Jul. Supplement 1981, pp. 31s–40s.

Auth, D.C., "Animal Testing of Endoscopic Hemostasis with Lasers and Other Devices," Endoscopy, vol. 18, Supplement 2, May 1986, pp. 36–39.

McLean, A.J., "The Bovie Electrosurgical Current Generator—Some Underlying Principles and Results," Archives of Surgery, vol. 18, 1929, pp. 1863–1873.

McLean, A. J., "Characteristics of Adequate Electrosurgical Current,"American Journal of Surgery, vol. XVIII, No. 3, Feb. 16, 1932, pp. 417–441.

Wattiez, Arnaud et al., *Electrosurgery in Operative Endoscopy*, Blackwell Science Ltd., London, 1995, pp. 87–93, 155–163.

Farin, G., "Pneumatically Controlled Bipolar Cutting Instrument," End. Surg., 1993, pp. 1–3.

Muller, W., "The Advantages of Laparoscopic Assisted Bipolar High–Frequency Surgery," End. Surg., 1993, pp. 1–6.

Reidenbach, H. D., "Fundamentals of Bipolar High–Frequency Surgery" End. Surg. 1993, pp. 85–90.

Penketh, Richard et al., "Clinical Evaluation of the Procision Bipolar Electrosurgical Generator During Laparoscopic Gynaecological Procedures," EAES, $2^{nd}$ International Congress of the European Association for Endoscopic Surgery, Madrid, Sep. 15–17, 1994.

Lloyd, David M. et al., "A New Portable Bipolar Generator–Use in Laparoscopic Cholecystectomy," EAES, $2^{nd}$ International Congress of the European Association for Endoscopic Surgery, Madrid, Sep. 15–17, 1994.

Buchelt, Martin et al., "Excimer Laser Ablation of Fibrocartilage: An In Vitro and In Vivo Study," Lasers in Surgery and Medicine, vol. 11, 1991, pp. 271–279.

Srinivasan, R., "Ablation of Polymers and Biological Tissue by Ultraviolet Lasers," Science, vol. 234, Oct. 31, 1986.

Pearce, John A., "Chapter 3 Electrosurgery," *Handbook of Biomedical Engineering*, Ed. Jacob Kline, Academic Press, Inc., 1988, pp. 99–113.

Selikowitz, Stuart M. et al., "Electric Current and Voltage Recordings on the Myocardium During Electrosurgical Procedures in Canines," *Reprint from Surgery, Gynecology & Obstetrics*, Mar. 1987, vol. 164, pp. 219–224.

Tucker, Robert D. et al., "Demodulated Low Frequency Currents from Electrosurgical Procedures," Surgery, Gynecology & Obstetrics, Jul. 1984, vol. 159, pp. 39–43.

Lu, David Y. et al., "Electrical Thermal Angioplasty: Catheter Design Features, In Vitro Tissue Ablation Studies and In Vivo Experimental Findings," Am J Cardiol, vol. 60, 1987, pp. 1117–1122.

Malis, Leonard I., "Electrosurgery: Technical Note," J. Neurosurg., vol. 85, 1996, pp. 970–975.

Slager, C. J. et al., "Spark Erosion of Arteriosclerotic Plaques," Kardiologie, vol. 76, Suppl. 6, 1987, pp. 67–71.

Geddes, Leslie A., *Medical Device Accidents —With Illustrative Cases*, CRC Press, New York, 1998, p. 93 (commentary on Honig, William M., "The Mechanism of Cutting in ELectrosurgery," IEEE Transactions on Biomedical Engineering, Jan. 1975, pp. 58–65.

Valleylab, Inc., "Force Electrosurgical Generators Instruction Manual," Valleylab Part No. 945 110 039 A, Feb. 1987, pp. 59–62.

Valleylab, Inc., "Advances in Bipolar Electrosurgery for Laparoscopic Surgery," Advances in Bipolar Electrosurgery, pp. 1–4.

Description of Codman and Johnson & Johnson Malis CMC–III Bipolar System.

Pfizer/Valleylab Press Release "Valleylab Inc. Introduces The Procision Bipolar Electrosurgery System," Sep. 15, 1994.

ArthroCare Corporation, "ArthroCare Arthroscopic Electrosurgery System, Model 970 Operator's Manual," Feb. 1996.

* cited by examiner

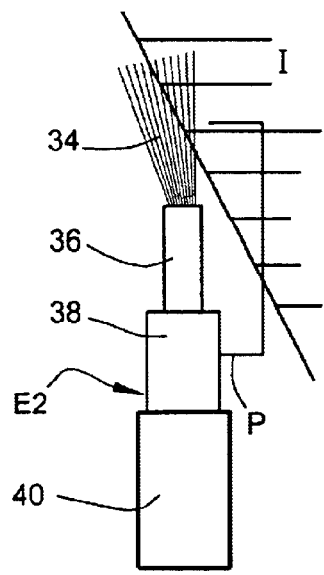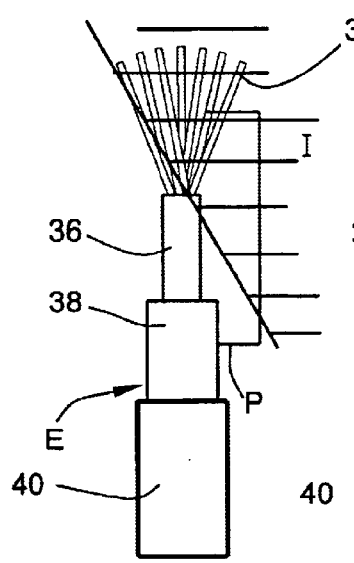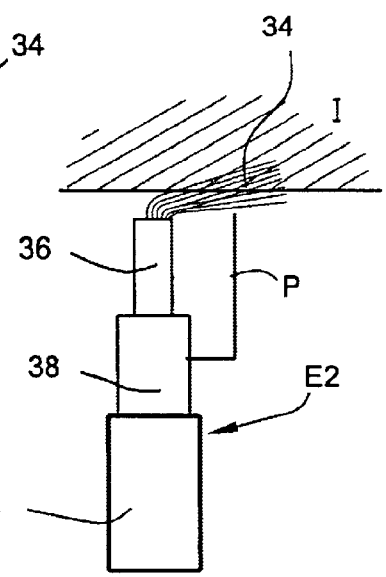
Fig. 5a    Fig. 5b    Fig. 5c
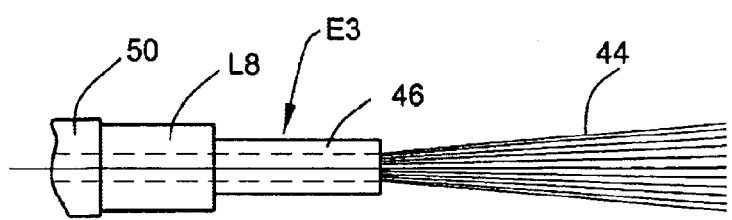
Fig. 6a

ELECTROSURGICAL INSTRUMENT

This is a continuation-in-part of U.S. patent application Ser. No. 09/318,615, filed on May 26, 1999, now U.S. Pat. No. 6,174,308, which is a divisional application of U.S. patent application Ser. No. 08/737,302, filed on Oct. 21, 1996, now U.S. Pat. No. 6,027,501, which is a 371 of PCT/GB96/01472 filed Jun. 20, 1996 and this application is additionally a continuation-in-part of U.S. patent application Ser. No. 09/198,396, filed on Nov. 24, 1998 now abandoned, a continuation of U.S. patent application Ser. No. 08/701,811, filed on Aug. 21, 1996, now U.S. Pat. No. 6,015,406 the entire content of which is hereby incorporated by reference in this application.

This invention relates to an electrosurgical instrument for the treatment of tissue in the presence of an electrically conductive fluid medium, to electrosurgical apparatus including such an instrument, and to an electrode unit for use in such an instrument. Endoscopic electrosurgery is useful for treating tissue in cavities of the body, and is normally performed in the presence of a distension medium. When the distension medium is a liquid, this is commonly referred to as underwater electrosurgery, this term denoting electrosurgery in which living tissue is treated using an electrosurgical instrument with a treatment electrode or electrodes immersed in liquid at the operation site. A gaseous medium is commonly employed when endoscopic surgery is performed in a distensible body cavity of larger potential volume in which a liquid medium would be unsuitable, as is often the case in laparoscopic or gastroenterological surgery.

Underwater surgery is commonly performed using endoscopic techniques, in which the endoscope itself may provide a conduit (commonly referred to as a working channel) for the passage of an electrode. Alternatively, the endoscope may be specifically adapted (as in a resectoscope) to include means for mounting an electrode, or the electrode may be introduced into a body cavity via a separate access means at an angle with respect to the endoscope—a technique commonly referred to as triangulation. These variations in technique can be subdivided by surgical speciality, where one or other of the techniques has particular advantages given the access route to the specific body cavity. Endoscopes with integral working channels, or those characterised as resectoscopes, are generally employed when the body cavity may be accessed through a natural opening—such as the cervical canal to access the endometrial cavity of the uterus, or the urethra to access the prostate gland and the bladder. Endoscopes specifically designed for use in the endometrial cavity are referred to as hysteroscopes, and those designed for use in the urinary tract include cystoscopes, urethroscopes and resectoscopes. The procedures of transurethal resection or vaporisation of the prostate gland are known as TURP and EVAP respectively. When there is no natural body opening through which an endoscope may be passed, the technique of triangulation is commonly employed. Triangulation is commonly used during underwater endoscopic surgery on joint cavities such as the knee and the shoulder. The endoscope used in these procedures is commonly referred to as an arthroscope.

Electrosurgery is usually carried out using either a monopolar instrument or a bipolar instrument. With monopolar electrosurgery, an active electrode is used in the operating region, and a conductive return plate is secured to the patient's skin. With this arrangement, current passes from the active electrode through the patient's tissues to the external return plate. Since the patient represents a significant portion of the circuit, input power levels have to be high (typically 150 to 250 watts), to compensate for the resistive current limiting of the patient's tissues and, in the case of underwater electrosurgery, power losses due to the fluid medium which is rendered partially conductive by the presence of blood or other body fluids. Using high power with a monopolar arrangement is also hazardous, due to the tissue heating that occurs at the return plate, which can cause severe skin burns. There is also the risk of capacitive coupling between the instrument and patient tissues at the entry point into the body cavity.

When performing surgery in body cavities, vital structures often lie in close proximity to the site of application, and these structures may be damaged by the collateral spread of the electrosurgical effect. Also of concern when using monopolar electrosurgery is that the operating voltage is elevated to overcome the resistive current limiting of the patient's tissues or to overcome carbonisation of the application electrode. Arcing by direct coupling to adjacent structures, or through breaches in insulation, may produce accidental tissue damage outside the narrow field of view of the endoscope. There is also the risk of capacitive coupling between the instrument and the patient's tissues at the entry point into the body cavity such that an electrosurgical energy may be coupled to tissue at the entry point. This coupled energy can sometimes be sufficient to cause burning. These risks of using monopolar electrosurgery during endoscopic procedures are now well recognised, and have driven a move towards adoption of bipolar surgery.

With bipolar electrosurgery, a pair of electrodes (an active electrode and a return electrode) are used together at the tissue application site. This arrangement has advantages from the safety standpoint, due to the relative proximity of the two electrodes so that radio frequency currents are limited to the region between the electrodes. However, the depth of effect is directly related to the distance between the two electrodes; and, in applications requiring very small electrodes, the inter-electrode spacing becomes very small, thereby limiting tissue effect and output power. Spacing the electrodes further apart would often obscure vision of the application site, and would require a modification in surgical technique to ensure correct contact of both electrodes with tissue.

There are a number of variations to the basic design of the bipolar probe. For example, U.S. Pat. No. 4,706,667 describes one of the fundamentals of the design, namely that the ratio of the contact areas of the return electrode and of the active electrode is greater than 7:1 and smaller than 20:1 for cutting purposes. This range relates only to cutting electrode configurations. When a bipolar instrument is used for desiccation or coagulation, the ratio of the contact areas of the two electrodes may be reduced to approximately 1:1 to avoid differential electrical stresses occurring at the contact between the tissue and the electrodes.

The electrical junction between the return electrode and the tissue can be supported by wetting of the tissue by a conductive solution such as normal saline. Both monopolar and bipolar probe arrangements often provide a means of suction and irrigation, primarily intended to wash the operative site. In such a case, the active electrode is retracted within the irrigation sheath to enable direct contact of the sheath with the tissue without the risk of mechanical damage to the tissue by the exposed electrode. No surgical effect can be produced with the electrode retracted, or during the passage of saline. As a secondary benefit, this arrangement allows the wetting of tissue to reduce contact impedance.

In bipolar needle arrangements, one of the obvious limitations is that the active electrode must be completely buried in the tissue to enable the return electrode to complete the circuit. Another problem is one of orientation: even a relatively small change in application angle from the ideal perpendicular contact with respect to the tissue surface, will change the electrode contact area ratio, so that a surgical effect can occur in the tissue contacting the return electrode.

Cavity distension provides space for gaining access to the operation site, to improve visualisation, and to allow for manipulation of instruments. In low volume body cavities, particularly where it is desirable to distend the cavity under higher pressure, liquid rather than gas is more commonly used due to better optical characteristics, and because it washes blood away from the operative site.

Conventional underwater electrosurgery has been performed using a non-conductive liquid (such as 1.5% glycine) as an irrigant, or as a distension medium to eliminate electrical conduction losses. Glycine is used in isotonic concentrations to prevent osmotic changes in the blood when intra-vascular absorption occurs. In the course of an operation, veins may be severed, with resultant infusion of the liquid into the circulation, which could cause, among other things, a dilution of serum sodium which can lead to a condition known as water intoxication.

The applicants have found that it is possible to use a conductive liquid medium, such as normal saline, in underwater endoscopic electrosurgery in place of non-conductive, electrolyte-free solutions. Normal saline is the preferred distension medium in underwater endoscopic surgery when electrosurgery is not contemplated, or a non-electrical tissue effect such as laser treatment is being used. Although normal saline (0.9% w/v; 150 mmol/l) has an electrical conductivity somewhat greater than that of most body tissue, it has the advantage that displacement by absorption or extravasation from the operative site produces little physiological effect, and the so-called water intoxication effects of non-conductive, electrolyte-free solutions are avoided.

Carbon dioxide is the preferred gaseous distension medium, primarily because of its non-toxic nature and high water solubility.

In endoscopic procedures in which the distension medium is a gas, the applicants have found that it is possible to use an electrically-conductive gas (such as argon) in place of carbon dioxide. Argon is conductive when excited into a discharge state, and has been employed in both endoscopic and conventional monopolar electrosurgery as a method of increasing the distance between the tissue and the instrument, by providing a conductive path between the two when high voltage electrosurgical ouputs such as spray or fulgurate are being used. The high voltages used in this application result in a very low penetration of the electrosurgical effect into the tissue, making the technique only suitable to control bleeding from multiple small blood vessels. This allows the surgeon to stanch bleeding from multiple sites in a surgical wound using a rapid "painting" technique, rather than applying electrosurgery to each individual bleeding site. The argon gas is delivered through a hollow surgical instrument, and passes over the monopolar electrode exposed at the tip of the instrument as a stream. This produces a region at the operative site which is rich in argon, and which contributes to the distension of the body cavity. High voltage monopolar electrosurgical outputs are undesirable in endoscopic surgery, because of the risks of damaging structures outside the field of vision, by either capacitive or direct coupling to a portion of the instrument remote from the operative site often outside the field of vision of the operator.

The applicants have developed a bipolar instrument suitable for underwater electrosurgery using a conductive liquid or gaseous medium. This electrosurgical instrument for the treatment of tissue in the presence of a fluid medium, comprises an instrument body having a handpiece and an instrument shaft and an electrode assembly, at one end of the shaft. The electrode assembly comprises a tissue treatment electrode which is exposed at the extreme distal end of the instrument, and a return electrode which is electrically insulated from the tissue treatment electrode and has a fluid contact surface spaced proximally from the exposed part of the tissue treatment electrode. In use of the instrument, the tissue treatment electrode is applied to the tissue to be treated whilst the, return electrode, being spaced proximally from the exposed part of the tissue treatment electrode, is normally spaced from the tissue and serves to complete an electrosurgical current loop from the tissue treatment electrode through the tissue and the fluid medium. This electrosurgical instrument is described in the specification of the applicants co-pending British Patent Application No. 9512889.8.

The electrode structure of this instrument, in combination with an electrically conductive fluid medium largely avoids the problems experienced with monopolar or bipolar electrosurgery. In particular, input power levels are much lower than those generally necessary with a monopolar arrangement (typically 100 watts). Moreover, because of the relatively large spacing between its electrodes, an improved depth of effect is obtained compared with conventional bipolar arrangement.

The aim of a first aspect of the invention is to provide an improved electrosurgical instrument of this type.

The present invention provides an electrosurgical instrument for the treatment of tissue in the presence of an electrically-conductive fluid medium, the instrument comprising an instrument shaft, and an electrode assembly at one end of the shaft, the electrode assembly comprising a tissue treatment electrode and a return electrode which is electrically insulated from the tissue treatment electrode by means of an insulation member, the tissue treatment electrode being exposed at the distal end portion of the instrument, and the return electrode having a fluid contact surface spaced proximally from the exposed end of the tissue treatment electrode by the insulation member, wherein the exposed end of the tissue treatment electrode is constituted by a plurality of tissue treatment filamentary members made of an electrically-conductive material, the filamentary members being electrically connected to a common electrical supply conductor.

The return electrode is spaced from the tissue treatment electrode so that, in use, it does not contact the tissue to be treated, and so that the electrical circuit is always completed by the conductive fluid, and not simply by arcing between the electrodes. Indeed, the arrangement is such that arcing between the adjacent parts of the electrode assembly is avoided, thereby ensuring that the tissue treatment electrode can become enveloped in a vapour pocket so that tissue entering the vapour pocket becomes the preferred path for current to flow back to the return electrode via the conductive fluid, In a preferred embodiment, a plurality of separate, individual filaments constitute the filamentary members. Advantageously, the filaments each have a length lying within the range of from 0.5 mm to 5 mm, in which case the instrument is used for tissue removal by vaporisation. Preferably, the filaments each have a diameter lying within the range of from 0.05 mm to 0.3 mm.

Alternatively, a single coiled filament constitutes the filamentary members, the coils of the filament constituting the filamentary members.

Preferably, the filamentary members extend longitudinally from the extreme distal end of the instrument. Alternatively, the filamentary members extend laterally through a cut-out formed in a side surface of the insulation member adjacent to the distal end thereof. Conveniently, the return electrode is formed with a hood-like extension which extends over the surface of the insulation member which is opposite the cut-out.

In another preferred embodiment, the filamentary members are mounted within the insulation member in such a manner that they are axially movable relative to the insulation member between a first operating position, in which they extend partially from the insulation member, and a second operating position, in which they extend fully from the insulation member. In this case, the instrument can be used for tissue removal by vaporisation when the filaments are in the first operating position, and for desiccation when the filaments are in the second operating position.

Advantageously, the common electrical supply conductor is a central conductor, the insulation member surrounding the central conductor.

The filamentary members may be made from a precious metal such as platinum or from a platinum alloy such as platinum/iridium, platinum/tungsten or platinum/cobalt. The filamentary members could also be made of tungsten. The insulation member may be made of a ceramic material, silicone rubber or glass.

Where the filamentary members are separate individual filaments, they may each have a length lying within the range of from 5 mm to 10 mm. In this case, they may be made of stainless steel.

In yet another preferred embodiment, the insulation member is formed with at least one wing, the or each wing extending distally from the insulation member to project beyond the tissue treatment electrode. Preferably, the insulation member is formed with a pair of diametrically-opposed wings.

The invention also provides an electrode unit for an electrosurgical instrument for the treatment of tissue in the presence of an electrically-conductive fluid medium, the electrode unit comprising a shaft having at one end means for connection to an instrument handpiece, and, mounted on the other end of the shaft, an electrode assembly comprising a tissue treatment electrode and a return electrode which is electrically insulated from the tissue treatment electrode by means of an insulation member, the tissue treatment electrode being exposed at the distal end portion of the instrument, and the return electrode having a fluid contact surface spaced proximally from the exposed end of the tissue treatment electrode by the insulation member, wherein the exposed end of the tissue treatment electrode is constituted by a plurality of tissue treatment filamentary members made of an electrically-conductive material, the filamentary members being electrically connected to a common electrical supply conductor.

The invention further provides electrosurgical apparatus comprising a radio frequency generator and an electrosurgical instrument for the treatment of tissue in the presence of an electrically-conductive fluid medium, the instrument comprising an instrument shaft, and an electrode assembly at one end of the shaft, the electrode assembly comprising a tissue treatment electrode and a return electrode which is electrically insulated from the tissue treatment electrode by means of an insulation member, the tissue treatment electrode being exposed at the distal end portion of the instrument, the return electrode having a fluid contact surface spaced proximally from the exposed end of the tissue treatment electrode by the insulation member, and the radio frequency generator having a bipolar output connected to the electrodes, wherein the exposed end of the tissue treatment electrode is constituted by a plurality of tissue treatment filamentary members made of an electrically-conductive material, the filamentary members being electrically connected to the radio frequency generator by a common electric supply conductor.

Electrosurgical instruments of the invention are useful for dissection, resection, vaporisation, desiccation and coagulation of tissue and combinations of these functions with particular application in hysteroscopic surgical procedures. Hysteroscopic operative procedures may include: removal of submucosal fibroids, polyps and malignant neoplasms; resection of congenital uterine anomalys such as septum or subseptum; division of synechiae (adhesiolysis); ablation of diseased or hypertrophic endometrial tissue; and haemostasis.

The instruments of the invention are also useful for dissection, resection, vaporisation, desiccation and coagulation of tissue and combinations of these functions with particular application in arthroscopic surgery as it pertains to endoscopic and percutaneous procedures performed on joints of the body including, but not limited to, such techniques as they apply to the spine and other non-synovial joints. Arthroscopic operative procedures may include: partial or complete meniscectomy of the knee joint including meniscal cystectomy; lateral retinacular release of the knee joint; removal of anterior and posterior cruciate ligaments or remnants thereof; labral tear resection, acromioplasty, bursectomy and subacromial decompression of the shoulder joint; anterior release of the temperomandibular joint; synovectomy, cartilage debridement, chondroplasty, division of intra-articular adhesions, fracture and tendon debridement as applied to any of the synovial joints of the body; inducing thermal shrinkage of joint capsule as a treatment for recurrent dislocation, subluxation or repetitive stress injury to any articulated joint of the body; disectomy either in the treatment of disc prolpase or as part of a spinal fusion via a posterior or anterior approach to the cervical, thoracic and lumbar spine or any other fibrous joint for similar purposes; excision of diseased tissue; and haemostasis.

The instruments of the invention are also useful for dissection, resection, vaporisation, desiccation and coagulation of tissue and combinations of these functions with particular application in urological endoscopic (urethroscopy, cystoscopy, ureteroscopy and nephroscopy) and percutaneous surgery. Urological procedures may include: electro-vaporisation of the prostate gland (EVAP) and other variants of the procedure commonly referred to as transurethral resection of the prostate (TURP) including, but not limited to, interstitial ablation of the prostate gland by a percutaneous or peruretheral route whether performed for benign or malignant disease; transurethral or percutaneous resection of urinary tract tumours as they may arise as primary or secondary neoplasms and further as they may arise anywhere in the urological tract from the calyces of the kidney to the external urethral meatus; division of strictures as they may arise at the pelviureteric junction (PUJ), ureter, ureteral orifice, bladder neck or urethra; correction of ureterocoele; shrinkage of bladder diverticular; cystoplasty procedures as they pertain to corrections of voiding dysfunction; thermally induced shrinkage of pelvic floor as a corrective treatment for bladder neck descent excision of diseased tissue; and haemostasis.

Surgical procedures using the instrument of the invention include introducing the electrode assembly to the surgical site through an artificial conduit (a cannula), or through a natural conduit which may be in an anatomical body cavity or space or one created surgically. The cavity or space may be distended during the procedure using a fluid or may be naturally held open by anatomical structures. The surgical site may be bathed in a continuous flow of conductive fluid such as saline solution to fill and distend the cavity. The procedures may include simultaneous viewing of the site via an endoscope or using an indirect visualisation means.

Yet a further aspect of the invention provides an irrigated bipolar electrosurgical instrument that can be used in open air or gas-filled environments, in body fluids, or by insertion into tissue by the creation of a conductive fluid environment around the tip of the instrument.

Accordingly, the present invention provides an electrosurgical instrument for the treatment of tissue in the presence of an electrically-conductive fluid, the instrument comprising an instrument shaft and an electrode assembly at one end of the shaft, the electrode assembly comprising a tissue treatment electrode and a return electrode which is electrically insulated from the tissue treatment electrode by means of an insulation member, the tissue treatment electrode being exposed at the extreme distal end of the instrument, and the return electrode having a fluid contact surface spaced from the exposed end of the tissue treatment electrode by the insulation member, wherein the instrument further comprises feed means for feeding electrically-conductive fluid to the region of the exposed end of the tissue treatment electrode in such a manner as to define a conductive fluid path that completes, in use, an electrical circuit between the tissue treatment electrode and the return electrode.

In this way, it is possible to create a local conductive fluid environment around the tip of an electrosurgical instrument by delivering the fluid through the instrument in such a manner that the return electrode can be positioned remote from the tissue treatment electrode on or within the shaft of the instrument.

The electrode structure of this instrument thus simulates a monopolar configuration, with one active (tissue treatment) electrode and a remote return electrode, the return electrode being positioned on the instrument shaft to provide all the safety advantages of bipolar electrosurgery without the drawbacks. The separation of the two electrodes is supported by the delivery of the conductive medium, and allows higher powers to be delivered compared to conventional bipolar electrosurgery, but yet at power levels lower than conventional monopolar electrosurgery. The arrangement can also produce a contact vaporisation of tissue comparable to that of laser surgery.

The return electrode is spaced from the tissue treatment electrode so that, in use, it does not contact the tissue to be treated, and so that the electrical circuit is always completed by the conductive fluid, and not simply by arcing between the electrodes. Indeed, the arrangement is such that arcing between adjacent parts of the electrode assembly is avoided, thereby ensuring that the tissue treatment electrode can become enveloped in a vapour pocket so that tissue entering the vapour pocket becomes the preferred path for current to flow back to the return electrode via the conductive fluid.

In a preferred embodiment, the instrument further comprises removal means for removing electrically conductive fluid from the region of the exposed end of the tissue treatment electrode. The removal means is particularly important when the conductive fluid is a liquid such as saline, as saline heated up by the electrosurgical output needs to be removed to prevent the risk of collateral tissue damage.

By continually feeding electrically-conductive fluid such as saline to the region of the tissue treatment (active) electrode, and continually removing the fluid from this region, it is possible to create a local fluid field at the active electrode. Moreover, as fluid is constantly replenished in this region, the temperature of the active electrode can be maintained at a desired level.

In a preferred embodiment, the return electrode is a tubular member which is coated with an insulating sheath, the coated return electrode constituting the instrument shaft. Advantageously, the inner surface of the tubular member constitutes the return electrode. Preferably, the tubular member is made of stainless steel. In this case, the tissue treatment electrode may be supported centrally within the tubular member by an insulating spacer. Conveniently, the insulating spacer is made of a ceramic material, silicone rubber or glass.

The instrument may further comprise a tube extending proximally of the spacer. Preferably, the feed channel is constituted by the annular space between the return electrode and the tube, and the return channel is constituted by the interior of the tube and aperture means extending through the spacer. Alternatively, the instrument may further comprise a second return electrode constituted by a second tubular stainless steel member positioned concentrically within the first-mentioned tubular stainless steel member. In this case, the feed channel may be constituted by the annular space between the two return electrodes, and the return channel is constituted by the annular space between the second return electrode and the tube.

The invention also provides electrosurgical apparatus comprising a radio frequency generator and an electrosurgical instrument for treatment of tissue in the presence of an electrically-conductive fluid medium, wherein the electrosurgical instrument is as defined above.

The electrosurgical instrument of this aspect of the invention is useful for dissection, resection, vaporisation, dessication and coagulation of tissue and combinations of these functions with particular application in laparascopic, colposcopic (including vaginal speculum) and open surgical procedures on the female genital tract and adnexal related diseases. Laparascopic operative procedures may include: removal of subserosal and pedunculated fibroids, ablation of ectopic endometrium, ovarian cystectomy and ovarian drilling procedures; oophorectomy, salpingo-oophorectomy, subtotal hysterectomy and laparaoscopically assisted vaginal hysterectomy (LAVH) as may be performed for benign or malignant diseases; laparoscopic uterosacral nerve ablation (LUNA); fallopian tube surgery as correction of ectopic pregnancy or complications arising from acquired obstructions; division of abdominal adhesions; and haemostasis.

The electrosurgical instrument of the invention is also useful in the lower female genital tract, including treatment of cervix, vagina and external genitalia whether accessed directly or using instrumentation comprising generally speculae and colposcopes. Such applications include: vaginal hysterectomy and other pelvic procedures utilising vaginal access; LLETZ/LEEP procedure (large loop excision of the transformation zone) or excision of the transformation zone of the endocervix; removal of cystic or septic lesions; ablation of genital or venereal warts; excision of benign and malignant lesions; cosmetic and surgical repairs including vaginal prolapse; excision of diseased tissue; and haemostasis.

The electrosurgical instrument of this aspect of the invention is also useful for dissection, resection, vaporisation, desiccation and coagulation of tissue and combinations of these functions with particular application in surgery on the ear nose and throat (ENT) and more particularly procedures performed on the oropharynx, nasopharynx and sinuses. These procedures may be performed through the mouth or nose using speculae or gags or using endoscopic techniques such as functional endoscopic sinus surgery (FESS). Functional endoscopic sinus procedures may include: removal of chronically-diseased, inflamed and hypertrophic mucus linings, polyps and neoplasms from the various anatomical sinuses of the skull; excision of diseased tissue; and haemostasis. Procedures on the nasopharynx may include: removal of chronically-diseased, inflamed and hypertrophic mucus linings, polyps and neoplasms from the turbinates and nasal passages; submucus resection of the nasal septum; excision of diseased tissue; and haemostasis. Procedures on the oropharynx may include: removal of chronically-diseased, inflamed and hypertrophic tissue, polyps and neoplasms particularly as they occur related to the tonsil, adenoid, epigloific and supra-glottic regions, and salivary glands; as an alternative method to perform the procedure commonly known as laser assisted uvulopalatoplasty (LAUP); excision of diseased tissue; and haemostasis.

It is evident from the scope of applications of the invention that it has further additional applications for dissection, resection, vaporisation, desiccation and coagulation of tissue and combinations of these functions in general lapaaroscopic, thoracoscopic and neurosurgical procedures, being particularly useful in the removal of diseased tissue and neoplastic disease whether benign or malignant.

Surgical procedures using the electrosurgical instrument of the invention include introducing the electrode assembly to the surgical site whether through an artificial (cannula) or natural conduit which may be in an anatomical body cavity or space or one created surgically either using the instrument itself or by another technique. The cavity or space may be distended during the procedure using a fluid, or may be naturally held open by anatomical structures. The surgical site may be bathed in a continuous flow of conductive fluid, such as saline solution, to create a locally-irrigated environment around the tip of the electrode assembly in a gas-filled cavity or on an external body surface or other such tissue surfaces exposed during part of a surgical procedure. The irrigating fluid may be aspirated from the surgical site to remove products created by application of the RF energy, tissue debris or blood. The procedures may include simultaneous viewing of the site via an endoscope or using an indirect visualisation means.

The invention further provides a method of operating an electrosurgical apparatus having at least at tissue desiccation mode and a tissue vaporisation mode, the apparatus having a radio frequency generator coupled to an electrode assembly for the treatment of tissue in the presence of an electrically-conductive fluid medium, the electrode assembly comprising a tissue treatment electrode and a return electrode which is electrically insulated from the tissue treatment electrode by means of an insulation member, the tissue treatment electrode being exposed at the extreme distal end of the assembly, the return electrode having a fluid contact surface spaced from the exposed end of the tissue treatment electrode by the insulation member, the method comprising the steps of:

feeding electrically-conductive fluid to the region of the exposed end of the tissue treatment electrode; and controlling the output power of the radio frequency generator to lie within a first output range for the tissue desiccation mode and to lie within a second range for the tissue vaporisation mode, the first output range being such that the power supplied to the electrode assembly maintains the conductive fluid adjacent to the tissue treatment electrode substantially at boiling point for tissue desiccation without creating a vapour pocket surrounding the tissue treatment electrode, and the second output range is such that the output power supplied to the electrode assembly for vaporisation of tissue is such as to maintain a vapour pocket surrounding the tissue treatment electrode.

Advantageously, the method further comprises the step of removing electrically-conductive fluid from the region of the exposed end of the tissue treatment electrode.

The invention still further provides an electrosurgical tissue desiccation method comprising the steps of:

providing an electrosurgical apparatus comprising a radio frequency generator coupled to an electrode assembly comprising a tissue treatment electrode and a return electrode, the tissue treatment electrode having an exposed distal end;

introducing the electrode assembly into a selected operation site with the tissue treatment electrode adjacent to the tissue to be treated;

feeding electrically-conductive fluid to the region of the exposed end of the tissue treatment electrode;

actuating the generator; and controlling the radio frequency power supplied to the electrode assembly by the generator to maintain the conductive fluid adjacent to the tissue treatment electrode substantially at its boiling point without creating a vapour pocket surrounding the tissue treatment electrode.

In this case, the return electrode may be spaced proximally with respect to the tissue treatment electrode, and the electrode assembly may be introduced into the selected operation site such that the tissue treatment electrode is in contact with the tissue to be treated, and the return electrode is immersed in the electrically-conductive fluid, the electrode assembly being manipulated to cause heating and desiccation of the tissue in a required region adjacent to the tissue treatment electrode. Preferably, the electrode assembly is manipulated by moving the tissue treatment electrode across the surface of the tissue to be treated in a side-to-side "painting" technique.

The invention also provides an electrosurgical method comprising the steps of:

providing an electrosurgical apparatus comprising a radio frequency generator coupled to an electrode assembly comprising a tissue treatment electrode and a return electrode, the tissue treatment electrode having an exposed distal end;

introducing the electrode assembly into a selected operation site with the tissue contact electrode adjacent to the tissue to be treated;

feeding electrically-conductive fluid to the region of the exposed end of the tissue treatment electrode;

actuating the generator; and applying sufficient radio frequency power to the electrode assembly to vaporise the electrically-conductive fluid surrounding the tissue treatment electrode to maintain a vapour pocket surrounding the tissue treatment electrode. Advantageously, the return electrode is spaced proximally with respect to the tissue treatment electrode, and the electrode assembly is introduced into the selected operation site'such that the tissue treatment electrode is positioned at least adjacent to the tissue to be treated, with the vapour pocket in contact with the tissue, and with the return electrode in contact with the electrically conductive fluid, the electrode structure being manipulated to achieve at least vaporisation of the tissue.

The invention will now be described in greater detail, by way of example with reference to the drawings, in which:

FIGS. 5a to 5c are diagrammatic side elevations of the electrode assembly of a second form of electrode unit constructed in accordance with the invention;

FIGS. 6a and 6b are diagrammatic side elevations of the electrode assembly of a third form of electrode unit constructed in accordance with the invention;

Each of the electrode units described below is intended to be used with a conductive distension medium such as normal saline, and each unit has a dual-electrode structure, with the conductive medium acting as a conductor between the tissue being treated and one of the electrodes, hereinafter called the return electrode. The other electrode is applied directly to the tissue, and is hereinafter called the tissue treatment (active) electrode. In many cases, the use of a liquid distension medium is preferable, as it prevents excessive electrode temperatures in most circumstances, and largely eliminates tissue sticking.

Figure 1:
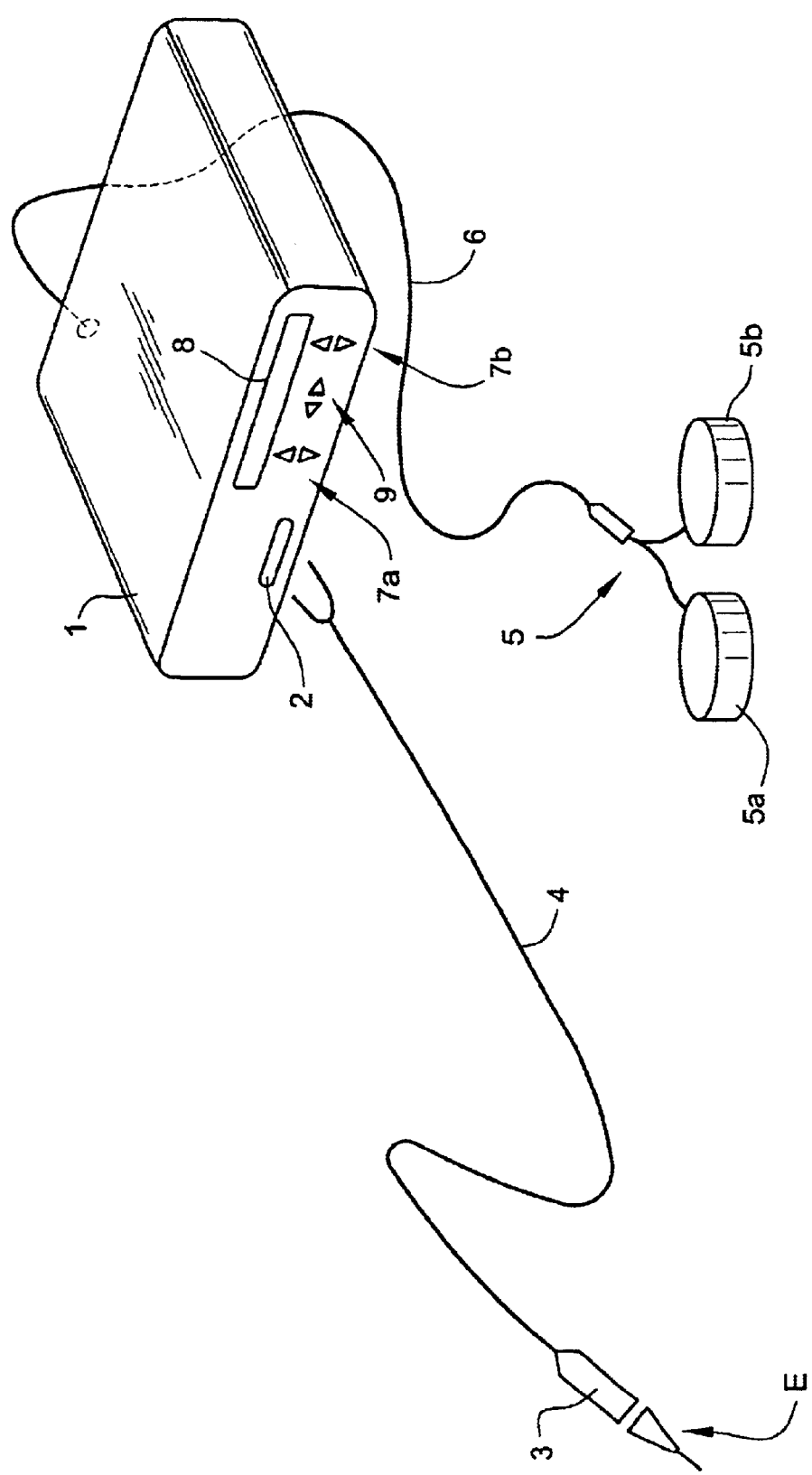
FIG. 1 is a diagram showing an electrosurgical apparatus constructed in accordance with the invention.

Referring to the drawings, FIG. 1 shows electrosurgical apparatus including a generator 1 having an output socket 2 providing a radio frequency (RF) output for an instrument in the form of a handpiece 3 via a connection cord 4. Activation of the generator 1 may be performed from the handpiece 3 via a control connection in the cord 4, or by means of a footswitch unit 5, as shown, connected separately to the rear of the generator 1 by a footswitch connection cord 6. In the illustrated embodiment, the footswitch unit 5 has two footswitches 5a and 5b for selecting a desiccation mode and a vaporisation mode of the generator 1 respectively. The generator front panel has push buttons 7a and 7b for respectively setting desiccation and vaporisation power levels, which are indicated in a display 8. Push buttons 9a are provided as an alternative means for selection between the desiccation and vaporisation modes.

The handpiece 3 mounts a detachable electrode unit E, such as the electrode units E1 to E11 to be described below.

Figure 2:
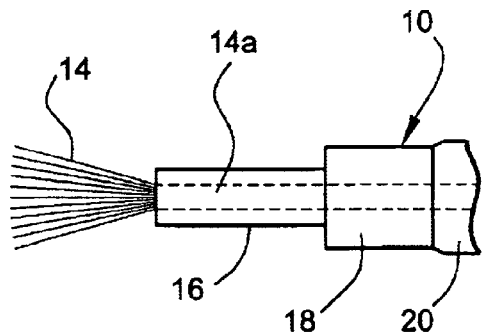
FIG. 2 is a diagrammatic side elevation of an electrode assembly at a distal end of a first form of electrode unit constructed in accordance with the invention.

FIG. 2 shows the first form of electrode unit E1 for detachable fastening to the electrosurgical instrument handpiece 3, the electrode unit comprising a shaft 10, which is constituted by a semi-flexible tube made of stainless steel or phynox electroplated in copper or gold, with an electrode assembly 12 at a distal end thereof. At the other end (not shown) of the shaft 10, means are provided for connecting the electrode unit E1 to a handpiece both mechanically and electrically.

The RF generator 1 delivers an electro-surgical current to the electrode assembly 12. The generator includes means for varying the delivered output power to suit different electrosurgical requirements. The generator may be as described in the specification of our co-pending British Patent Application 9512888.0.

The electrode assembly 12 includes a central, tissue treatment (active) electrode 14 in the form of a brush electrode. The active electrode 14 is connected to the generator 1 via an integral central conductor 14a and a central copper conductor (not shown) positioned within the handpiece of the instrument. The brush electrode 14 is constituted by a plurality of filaments of tungsten, the filaments having diameters lying in the range from 0.05 mm to 0.3 mm. A tapered ceramic insulation sleeve 16 surrounds the conductor 14a. A return electrode 18, which is constituted by the distal end portion of the shaft 10, abuts the proximal end of the sleeve 16. An outer insulating coating 20 surrounds the proximal portion of the shaft adjacent to the return electrode 18. The coating 20 would be polyvinylidene fluoride, a polyimide, polytetrafuoroethylene, a polyolefin, a polyester or ethylene tetrafluoroethylene.

Figure 3:
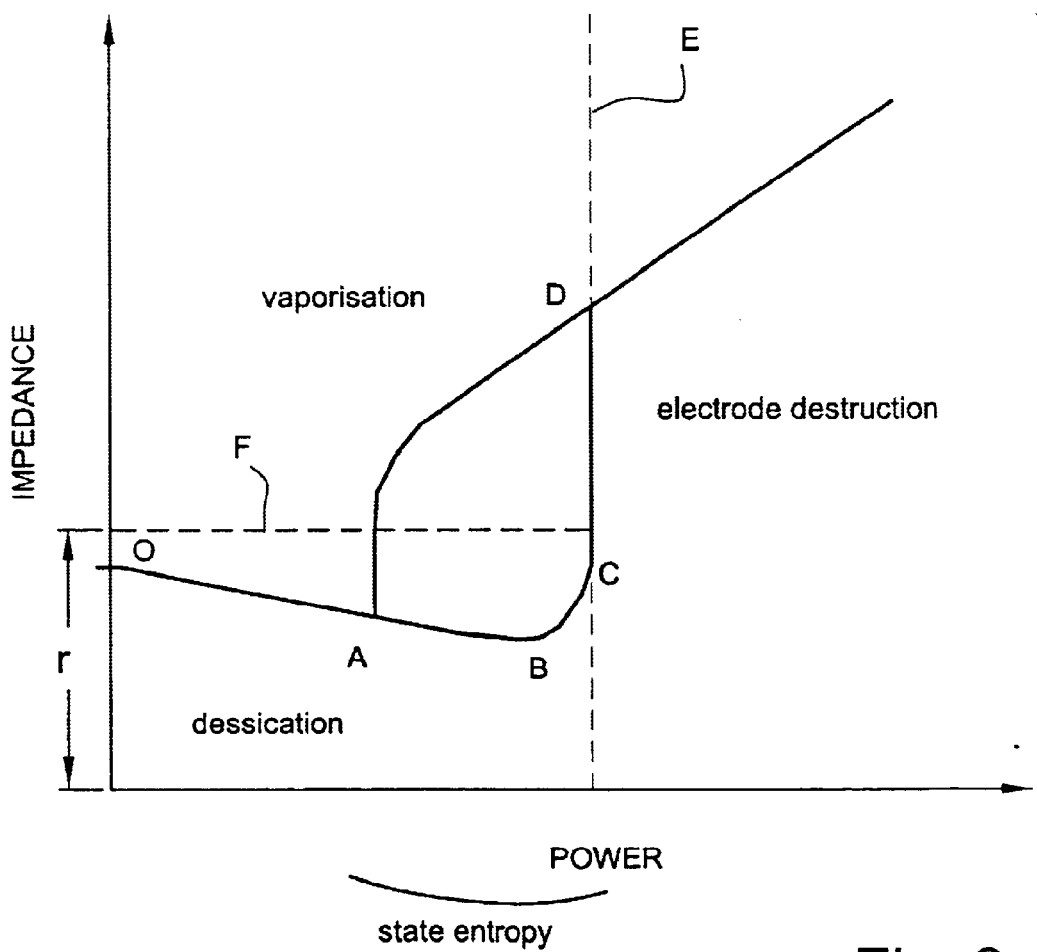
FIG. 3 is a graph illustrating the hysteresis which exists between the use of the electrode unit of FIG. 2 in desiccating and vaporising modes.

By varying the output of the generator 1, the electrode unit E1 of FIG. 2 can be used for tissue removal by vaporisation, or for desiccation. FIG. 3 illustrates how the RF generator 1 can be controlled to take advantage of the hysteresis which exists between the desiccation and the vaporising modes of the electrode unit E1. Thus, assuming the electrode assembly 12 of the unit E1 is immersed in a conductive medium such as saline, there is an initial impedance "r" at point "O", the magnitude of which is defined by the geometry of the electrode assembly and the electrical conductivity of the fluid medium. The value of "r" will change when the active electrode 14 contacts tissue, the higher the value of "r" the greater the propensity of the electrode assembly 12 to enter the vaporisation mode. When RF power is applied to the electrode assembly 12 the fluid medium heats up. Assuming the fluid medium is normal saline (0.9% w/v), the temperature coefficient of the fluid medium is positive, so that the corresponding impedance coefficient is negative. Thus, as power is applied, the impedance initially falls and continues to fall with increasing power to point "B", at which point the saline in intimate contact with the electrode assembly 12 reaches boiling point. Small vapour bubbles form on the surface of the active electrode 14 and the impedance then starts to rise. After point "B", as power is increased further, the positive power coefficient of impedance is dominant, so that increasing power now brings about increasing impedance.

As a vapour pocket forms from the vapour bubbles, there is an increase in the power density at the residual electrode/saline interface. There is, however, an exposed area of the active electrode 14 not covered by vapour bubbles, and this further stresses the interface, producing more vapour bubbles and thus even higher power density. This is a run-away condition, with an equilibrium point only occurring once the electrode is completely enveloped in vapour. For given set of variables, there is a power threshold before this new equilibrium can be reached (point "C").

The region of the graph between the points "B" and "C", therefore, represents the upper limit of the desiccation mode. Once in the vaporisation equilibrium state, the impedance rapidly increases to around 1000 ohms, with the absolute value depending on the system variables. The vapour pocket is then sustained by discharges across the vapour pocket between the active electrode 14 and the vapour/saline interface. The majority of power dissipation occurs within this pocket, with consequent heating of the active electrode 14. The amount of energy dissipation, and the size of the pocket, depends on the output voltage. If this is too low, the pocket will not be sustained, and if it is too high the electrode assembly 12 will be destroyed. Thus, in order to prevent destruction of the electrode assembly 12, the power output of the generator 1 must be reduced once the impedance has reached the point "D". It should be noted that, if the power is not reduced at this point, the power/impedance curve will continue to climb and electrode destruction would occur. The dotted line E indicates the power level above which electrode destruction is inevitable. As the power is reduced, the impedance falls until, at point "A", the vapour pocket collapses and the electrode assembly 12 reverts to the desiccation mode. At this point, power dissipation within the vapour pocket is insufficient to sustain it, so that direct contact between the active electrode 14 and the saline is re-established, and the impedance falls dramatically. The power density at the active electrode 14 also falls, so that the temperature of the saline falls below boiling point. The electrode assembly 12 is then in a stable desiccation mode. With the generator described in the specification of our co-pending British patent application 9604770.9, the output is 350 to 550 volts peak for the vaporisation mode, and about 170 volts peak for the desiccation mode.

It will be apparent that the electrode unit E1 of FIG. 2 can be used for desiccation by operating the unit in the region of the graph between the point "0" and a point in the region between the points "B" and "C". In this case, the electrode assembly 12 would be introduced into a selected operation site with the active electrode 14 adjacent to the tissue to be treated, and with the tissue, the active electrode and the return electrode 18 immersed in the saline. The RF generator 1 would then be activated (and cyclically controlled as described in the specification of our co-pending British patent application 9604770.9) to supply sufficient power to the electrode assembly 12 to maintain the saline adjacent to the active electrode 14 at, or just below, its boiling point without creating a vapour pocket surrounding the active tip. The electrode assembly would then be manipulated to cause heating and dessication of the tissue in a required region adjacent to the active electrode 14. The electrode unit E1 can be used for vaporisation in the region of the graph between the point "D" and the dotted line F which constitutes the level below which vaporisation cannot occur. The upper part of this curve is used for tissue removal by vaporisation. It should also be appreciated that the electrode unit E1 could be used for cutting tissue. In the cutting mode, the electrode unit E1 still operates with a vapour pocket, but this pocket is much smaller than that used for vaporisation, so that there is the least amount of tissue damage commensurate with cutting. Typically, the generator operates at about 270 volts peak for cutting.

The temperature generated at the active electrode 14 is of the order of 1500° C. in the vaporisation mode, so that the active electrode is made of a material that can withstand such high temperatures. Preferably, the active electrode 14 is made of tungsten, platinum or a platinum alloy (such as platinum/iridium or platinum/tungsten).

Figure 4A:
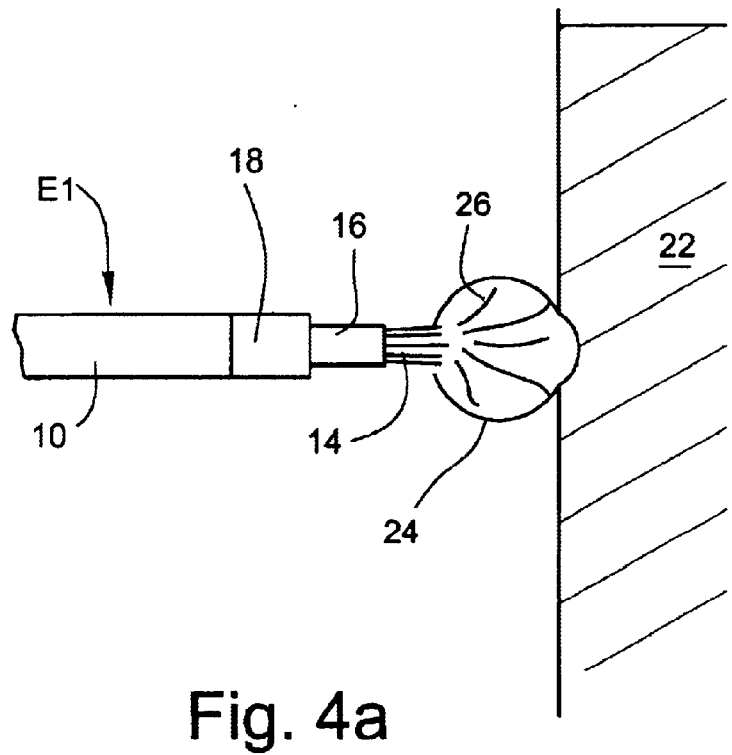
FIG. 4a is a diagrammatic side elevation of the first electrode unit, showing the use of such a unit for tissue removal by vaporisation.

FIG. 4a illustrates schematically the use of the electrode unit E1 of FIG. 2 for tissue removal by vaporisation. Thus, the electrode unit E1 creates a sufficiently high energy density at the active electrode 14 to vaporise tissue 22, and to create a vapour pocket 24 surrounding the active electrode. The formation of the vapour pocket 24 creates about a 10-fold increase in contact impedance, with a consequent increase in output voltage. Arcs 26 are created in the vapour pocket 24 to complete the circuit to the return electrode 18. Tissue 22 which contacts the vapour pocket 24 will represent a path of least electrical resistance to complete the circuit. The closer the tissue 22 comes to the active electrode 14, the more energy is concentrated to the tissue, to the extent that the cells explode as they are struck by the arcs 26, because the return path through the conductive fluid (saline in this case) is blocked by the high impedance barrier of the vapour pocket 24. The saline solution also acts to dissolve the solid products of vaporisation.

Figure 4B:
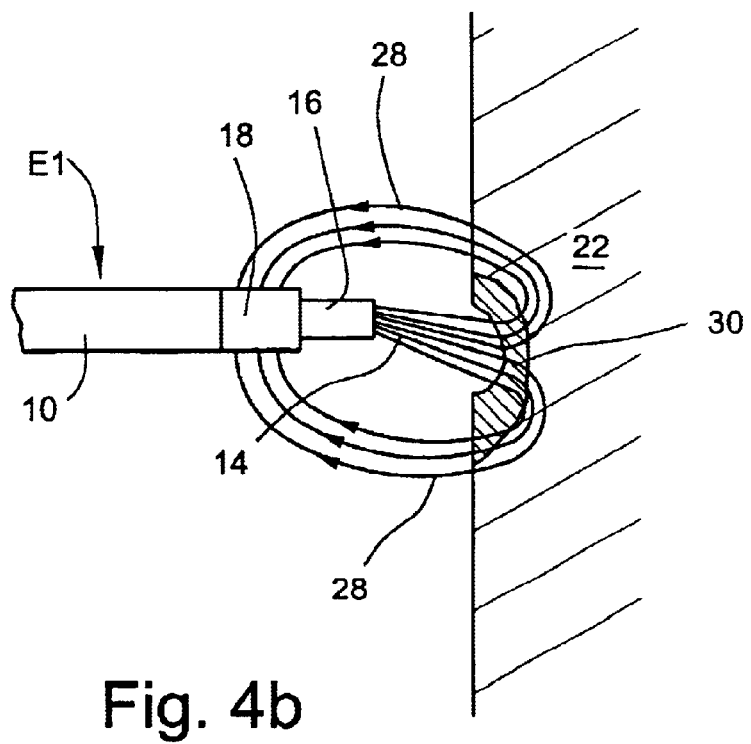
FIG. 4b is a diagrammatic side elevation of the first electrode unit, showing the use of such a unit for tissue desiccation.

FIG. 4b illustrates schematically the use of the electrode unit E1 for tissue desiccation. In the desiccation mode, output power is delivered to the electrode assembly 12 in a first output range, so that current flows from the active electrode 14 to become heated, preferably to a point at or near the boiling point of the saline solution. This creates small vapour bubbles on the surface of the active electrode 14 that increases the impedance about the active electrode.

The body tissue 22 typically has a lower impedance than the impedance of the combination of vapour bubbles and saline solution adjacent to the active electrode 14. When the active electrode 14 surrounded by small vapour bubbles and saline solution is brought into contact with the tissue 22, the tissue becomes part of the preferred lectrical current path. Accordingly, the preferred current path goes out of the active lectrode 14 at the point of tissue contact, through the tissue 22, and then back to the return electrode 18 via the saline solution, as shown by the current path lines 28 in FIG. 3b.

The invention has particular application in desiccating tissue. For tissue desiccating, one preferred approach is to contact only part of the active electrode 14 to the tissue 22, with the remainder of the active electrode remaining remote from the tissue and surrounded by saline solution, so that current can pass from the active electrode to the return electrode 18 via the saline solution, without passing through the tissue. For example, in the embodiment shown in FIG. 4b, only the distal portion of the active electrode 14 contacts the tissue 22, with the proximal portion remaining spaced away from the tissue.

The invention can achieve desiccation with no or minimal charring of the tissue 22. When the active electrode 14 contacts the tissue 22, current passes through the tissue, causing the tissue at, and around, the contact point to desiccate. The area and volume of desiccated tissue 30 expands generally radially outwardly from the point of contact. As the tissue 22 is desiccated, it loses its conductivity. As the area and volume of desiccated tissue 30 grows, a point is reached where the conductivity of the tissue is less than the conductivity of the heated saline solution surrounding the active electrode 14.

The current will prefer to follow the least-impedance path. Accordingly, as the impedance of the tissue 22 increases (due to desiccation) to a point where it approaches or exceeds the impedance of the combination of vapour bubbles and saline solution surrounding the active electrode 14, the preferred electrical current path will shift to a new path through the vapour bubbles and saline solution. Accordingly, once a large enough portion of tissue is desiccated, most (or substantially all) the current flow necessarily shifts to pass directly from the active electrode 14 into the saline solution. Before the tissue 22 becomes charred or scorched, the increased impedance of the desiccated tissue 30 causes most of the current to follow the path through the saline solution. No current, or a very small amount of current, will continue to pass through the desiccated tissue, and charring will be prevented.

In the embodiment shown in FIG. 4b, the exposed, stranded portion of the active electrode 14 allows parts of the active electrode to contact the tissue surface, while still maintaining most of the active electrode exposed portion out of contact with the tissue. Because most of the exposed portion of the active electrode 14 is out of contact with the tissue 22, the current path will more easily shift, upon desiccation of a sufficient tissue volume, from the path through the tissue to a path that goes directly from the active electrode to the saline solution.

When the electrode unit E1 is in the desiccation mode, the flexibility of the brush electrode 14 offers considerable advantages when working with small diameter electrodes in irregular body cavities in which large areas of tissue require desiccation. From a technical standpoint, the return:active ratio is variable from >1:1 in the "closed" form to <1:1 in the "splayed" form. This variability of the return:active ratio is explained in greater detail below with reference to FIGS. 5a to 5c.

FIG. 5 shows the second form of electrode unit E2 whose electrode assembly 32 includes an active electrode 34 which is constituted by a plurality of filaments made of a conductive material such as stainless steel. The filaments of the brush electrode 34 are much longer (10 mm as compared with 5 mm) than the filaments of the brush electrode 14, as the electrode unit E2 is intended primarily for desiccation. In this embodiment, the return:active ratio is variable from >2:1 in the "closed" form to <1:1 in the "splayed" form sleeve 36, a return electrode 38 and an outer insulating sheath 40. The active electrode 34 is a brush electrode whose tip is flexible to provide a reproducible tissue effect which is substantially independent of the application angle of the electrode with respect to the surface of the tissue T (see FIG. 5c). Thus, the flexibility of the active electrode 34 results in differential contact areas of the active electrode dependent on the applied pressure. For example, FIG. 5a shows the brush electrode 34 "closed" during the application of light pressure, and FIG. 5b shows the brush "splayed" by firm tissue pressure. This enables the creation of a broader surgical effect than the diameter of the electrode 34 would otherwise allow, thereby reducing treatment time. FIGS. 5a to 5c also show the return path P for the current flow from the active electrode 34 to the return electrode 38 via the conductive medium.

This large variation in the return:active ratio is a feature which cannot be supported by conventional bipolar designs. This variation in ratio can occur because the conductive path to complete the electrical circuit is maintained by the low impedance of the electrode contact with the conductive fluid operating medium. In order to sustain the low impedance transfer of RF energy to the tissues, the RF generator must be controlled in such a way that vapour pockets cannot form at the interface between the active electrode and the tissue. This allows the tissue contact to be continually wetted by the conductive fluid so that, whilst the tissue water is removed by thermal desiccation, the impedance reaches an upper limit determined by a point just below a voltage threshold above which vapour pockets will start to form. This, combined with the greater insulation separation between the active and return electrodes, enables this type of electrode unit to deliver much higher powers effectively to the tissue for a given electrode dimension than any known electrode unit.

Figure 6B:
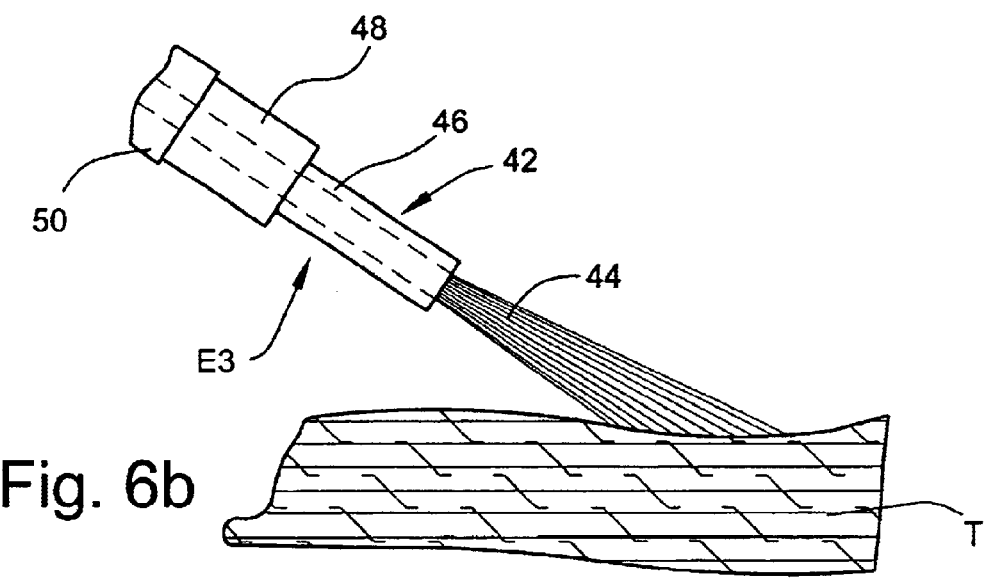

FIGS. 6a and 6b show the third form of electrode unit E3. This unit E3 is a modification of the electrode unit E2, and its electrode assembly 42 includes an active electrode 44 which is constituted by plurality of filaments made of stainless steel. The active electrode 44 is, therefore, a brush electrode and the filaments of this electrode are of a similar length to the filaments of the brush electrode 32. The electrode unit E3 is, therefore, intended primarily for desiccation. The electrode assembly 42 also includes a ceramic insulation sleeve 46, a return electrode 48 and an outer insulating sheath 50. The insulation sleeve 46 is made of a ceramic material and, like the insulation sleeve 16 of the electrode unit E1, it tapers towards the distal end of the electrode assembly 42. FIG. 6a shows the electrode unit E3 in a non-operational position, and FIG. 6b shows the unit in desiccating mode against tissue T.

Figures 7A, 7B:
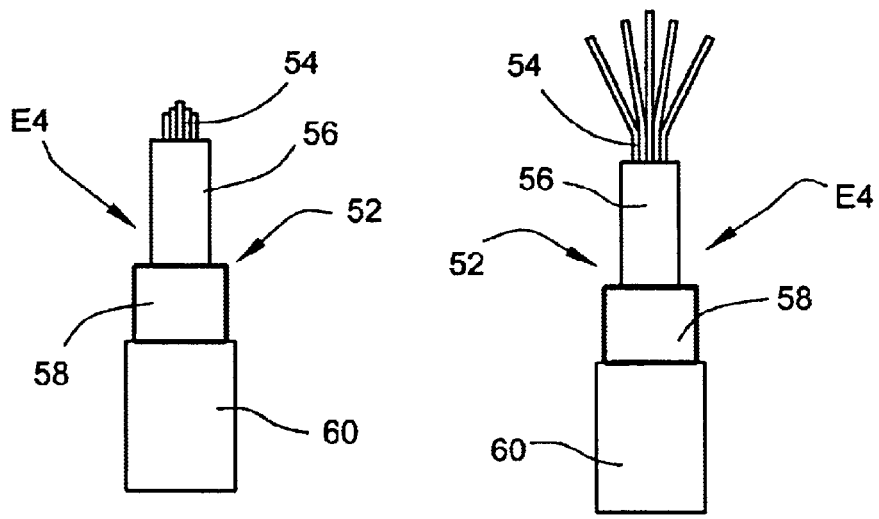
FIGS. 7a and 7b are diagrammatic side elevations of the electrode assembly of a fourth form of electrode unit constructed in accordance with the invention.

FIGS. 7a and 7b show a fourth form of electrode unit E4 whose electrode assembly 52 includes an extensible active electrode 54 in the form of a brush electrode. The filaments of the brush electrode 54 are made of tungsten, platinum, platinum/tungsten or platinum/iridium. The electrode unit E4 also includes a ceramic insulation sleeve 56, a return electrode 58, and an insulating sheath 60. As shown in FIG. 7a, the active electrode 54 can be withdrawn substantially within the insulation sleeve 56 so that only the free end portions of its filaments are exposed. With the active electrode 54 in this position, the electrode unit E4 can be used to vaporise tissue in the manner described above with reference to FIG. 4. On the other hand, if the active electrode 54 is extended (see FIG. 7b), so that its filaments extend fully from the distal end of the sleeve 56, the electrode unit E4 can be used for desiccation. The ratio of the contact areas of the return to active electrodes of the unit E4 can, therefore, be varied between the fully retracted active electrode position (in which the ratio is high and the unit is used for vaporisation), and the extended position (in which the ratio is low and the unit is used for desiccation). The unit E4 achieves its dual functionality by varying the extent by which the filaments of the active electrode 54 are extended. Dual functionality could also be achieved by varying axial separation between the active electrode 54 and the return electrode 58 (for example by varying the length of the insulation sleeve 56). With a large extension of the filaments of the active electrode 54 or with a large axial electrode separation, a large electric field is created, so that more tissue is affected. With no extension of the filaments of the active electrode 54 or with a reduced electrode separation, a smaller electric field is produced, and is used for cutting or vaporisation in circumstances where no collateral thermal damage to tissue is desirable. The larger electric field pattern is desirable for desiccation, or in circumstances where the desiccation of collateral tissue is desirable to prevent haemorrhage from a cut surface.

Depending upon the ratio of the return:active electrode area, therefore, the brush electrode of the invention can have a dessication function (as exemplified by the embodiments of FIGS. 5 and 6), a vaporisation function (as exemplified by the embodiment of FIG. 4), or a dual desiccation/vaporisation function (as exemplified by the embodiment of FIG. 7).

As indicated above, the primary use for the desiccating brush is in providing a flexible, broad area electrode for desiccating large irregular areas of tissue. The requirement to treat such areas occurs in hysteroscopic surgery—desiccation of the endometrial lining of the uterus, and in urological surgery—desiccation and shrinkage of bladder diverticular. In both instances, the electrode is introduced through the working channel of the endoscope.

Introduction of the desiccating brush with a long and flexible, filamentary structure can prove problematical when the working channel of the endoscope is angled or includes steps in the inner bore. This can deform the brush filaments which, once inserted, cannot be adjusted and may not conform to the area of tissue to be treated. Bending back of the filaments may also inadvertently create an electrical short to the return electrode.

Figure 8A:
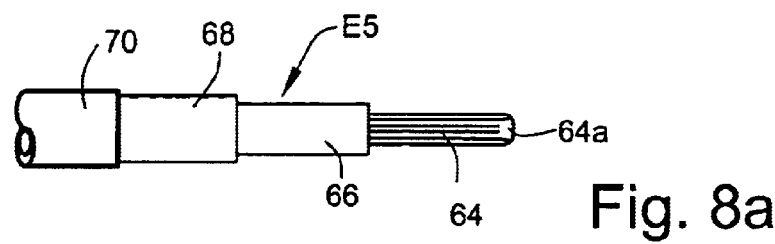
FIGS. 8a and 8b are diagrammatic side elevations of a fifth form of electrode unit constructed in accordance with the invention.
Figure 8B:
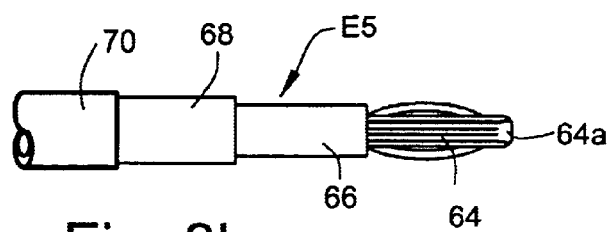

Whilst preserving the desired functions of flexibility and contact area geometry dependent on the pressure of application, the basic desiccating brush can be modified to overcome this problem. For example, the brush filaments can be simply tvisted together. Preferably, however, the filaments are welded together at their distal ends as shown in FIG. 8 which shows a fifth form of electrode unit E5. The electrode unit E5 includes an active electrode 64 in the form of a brush electrode whose filaments are made of platinum, platinum/tungsten or platinum/iridium. The distal ends 64$a$ of the filaments are welded together as shown in FIG. 8$a$. This prevents distortion of the filaments in the working channel of an endoscope, whilst permitting bowing of the filaments (as shown in FIG. 8$b$) to increase tissue contact area. The electrode unit E5 includes a ceramic insulation sleeve 66, a return electrode 68 and an outer insulating sleeve 70.

In the dual function brush electrode, the retum:active electrode area can be elevated to a level which is capable of producing tissue vaporisation. Obviously, with a very small active electrode area at the extreme of this range, the amount of tissue which can be desiccated becomes too small to be practically useful. If, however, the ratio is configured in the mid-range, then the same electrode can be used to produce both effective desiccation and tissue removal by vaporisation. The short brush described in FIG. 2 is one example of such a dual purpose electrode. Given that the filaments cannot be fabricated in stainless steel to support vaporisation, tungsten filaments are the preferred material in the short brush due to their rigidity overcoming the issues of distortion during introduction. Platinum alloys withstand the high vaporisation temperatures better than tungsten but, due to their flexibility and the annealing process during use, cannot be used in the short brush form. Platinum alloy dual-function brush-type electrodes, therefore, require the modifications of twisting, braiding, or welding of the distal tips to prevent distortion.

These combined multi-functional brush electrode forms are particularly useful in removing tumour masses or polyps encountered during hysteroscopic and urological surgery. They can vaporise the tumour bulk, incise the stalks of polyps, and desiccate any bleeding vessels or the base of the tumour without the need to change electrodes.

In these multi-functional forms, the active electrode area is maximised for desiccation whilst still being capable of vaporisation or cutting functions. The minimum ratio depends on four important critera, namely:

1. The intrinsic impedance of the target tissue.
2. The volume of the body cavity.
3. The configuration of the active electrode.
4. The maximum output power from the RF generator.

The configuration of the active electrode obviously influences the ratio, with cylindrical forms representing the lowest ratio for a given length, but the other factors relate to the inability of the electrode to retain a vapour bubble. The filaments of the brush-type electrodes retain vapour bubbles, which helps maintain the vaporisation condition.

An arthroscope electrode may be characterised as short (100–140 mm), rigid with a working diameter up to 4 mm. It can be introduced through a stab incision into a joint cavity (with or without a cannula) using the triangulation technique. When an arthroscope includes a brush electrode of the type described above, it is operated with a motion which commonly moves the brush electrode between the 9 o'clock and 3 o'clock positions on the arthroscopic image. As a result, the tissue to be treated is commonly approached at a shallow working angle with respect to the axis of the electrode. The electrode for arthoscopy thus needs to have an effect consistent with this angled approach to the tissue. The tissue to be treated, such as meniscal cartilage, is commonly dense and of a high electrical impedance, such tissue having a free edge representing a common injury site where treatment is required. The drawback of known arthroscope electrodes which are solid form electrodes is that, because the joint spaces are commonly small (the joint spaces in the knee being typically 60–100 mls under fluid distension), the vapour bubbles generated are large and tend to cause problems with visualisation.

Because of the higher impedance of the target tissue, the arthroscopic multi-function brush electrode should support a lower ratio than electrodes designed for hysteroscopic and urological applications where the tissue is more vascular. Reducing the ratio does, however, have one drawback in body cavities of small volume, such as the knee joint which is typically 60–80 mls, and that is heating of the surrounded irrigant or distension fluid. Heating occurs primarily during the application of power to reach the vaporisation threshold. Once the threshold has been reached, the power requirement typically falls by 30–50%. Reducing the electrode ratio increases the power requirement to reach the threshold so that, despite the high impedance of the target tissue, it is undesirable to reduce the ratio to the lowest value capable of supporting vaporisation.

In addition, the high impedance is due to lack of vascularity of such tissues as meniscal cartilage. Except, therefore, when muscle or synovial tissue is being treated, the primary function of the athroscopic brush electrode is that it should provide rapid debulking of dense, avascular tissue. Desiccate functionality is not a requirement of such an instrument. Indeed, very short rigid brush electrodes with electrode ratios greater than 5:1 are desirable. The only reason for not elevating the ratio further is the need to engage the maximum amount of tissue and simultaneously reduce procedure time.

A short, rigid brush electrode (of the type described above with reference to FIG. 2 or FIG. 7$a$) can be thought of as an end-effect electrode which has tissue debulking precision with minimal thermal spread. Consequently, it can be used to create discrete holes in tissue, thereby to create an access channel to tissue deep to the surface, as may be required as part of an interstitial ablation technique on a tissue mass such as a prostate adenoma or a uterine fibroid (myolysis). This use of a vaporising, end-effect, technique enables only the fibroid to be removed by complete debulking leaving a resection margin conforming to the "false capsule" of the fibroid. No normal tissue is removed and, due to control of collateral thermal effects at the endometrial resection margin, the scarring is reduced to a minimum, thereby increasing what chances there were of restoring fertility. Additionally, of course, vaporisation does not produce resection chippings to interfere with visualisation and prolong the procedure through the need to wash them out once the resection is completed. Conventional loop electrode resectoscopes require removal of normal tissue surrounding such fibroids, and this is disadvantageous because it increases the chance of bleeding, the risk of uterine perforation and the scarring of the uterus. This latter aspect is particularly undesirable when the procedure is being performed in an attempt to restore fertility.

Alternatively, a short, rigid brush electrode can be used to debulk a tumour (such as a fibroid, a bladder tumour or a prostate adenoma), or it can be used with the multiple puncture or drilling technique. In this case, after removing the intrauterine portion, the intramural portion can be treated by creating ("drilling") a series of holes into the abnormal tissue whether, for example, this is a fibroid or prostatic adenoma. To assess the depth of penetration, marks may be provided on the electrode shaft at measured distances from the tip, and hence to compare the depth of penetration against the pre-operative results of tests performed to establish size of the tumour or adenoma. The residual tissue bridges will shrink as part of the healing process. Whilst not removing the whole tumour, this technique is safer and quicker than removing the entire fibroid or prostatic adenoma, when treatment is being performed either for menorrhagia or blader outflow obstruction, respectively.

Figure 9:
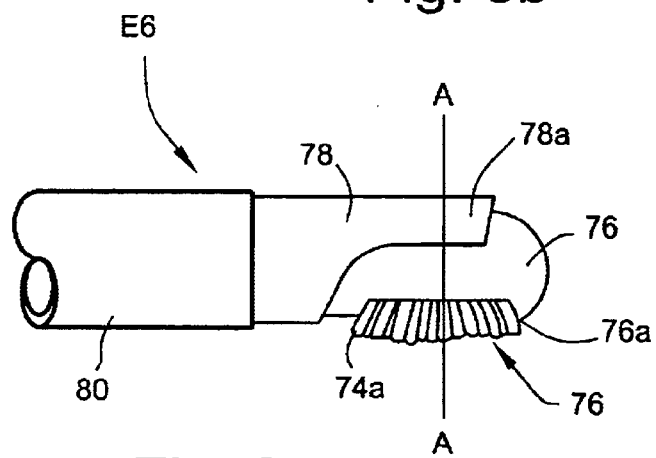
FIG. 9 is a diagrammatic side elevation of a sixth form of electrode unit constructed in accordance with the invention.

FIG. 9 shows an arthroscope electrode unit E6 constructed in accordance with the invention. The electrode unit E6 includes an active electrode 74 which is constituted by a plurality of filaments made of tungsten or an alloy of tungsten or platinum. The active (brush) electrode 74 is connected to an RF generator (not shown) via a central copper conductor (also not shown). A ceramic insulation sleeve 76 surrounds the central conductor, the filaments 74a of the brush electrode passing along the insulation sleeve and extending laterally therefrom through a cut-out 76a. A return electrode 78, which is constituted by the distal end of the instrument shaft, surrounds the proximal end of the sleeve 76. An outer insulating coating 80 (which would be polyvinylidene fluoride, a polyimide, polytetrafluoroethylene, a polyolefin, a polyester or ethylene tetrafluoroethylene) surrounds the proximal portion of the shaft adjacent to the return electrode 78. The return electrode 78 is formed with a hood-like extension 78a which extends over the surface of the sleeve 76 which is opposite to the cut-out 76a. The electrode unit E6 can, thus, provide maximum tissue engagement for shallow working angle applications, and is known as a side-effect electrode.

Figure 10:
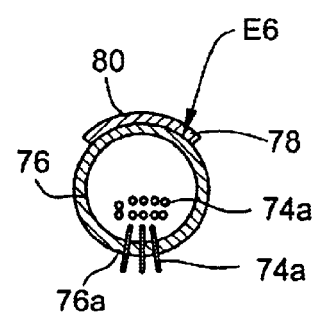
FIG. 10 is a cross-section taken on the line A—A of FIG. 9.

Another problem with working in the confined space of a joint cavity is in preventing damage to adjacent structures, particularly when the vaporising effect is enhanced, and both the tissue density and application angle make engagement and location difficult. This protection feature is intrinsic in the side-effect brush of FIG. 9, when the insulation sleeve 76 protects tissue above, below and behind the active electrode window 76a which only occupies a small arc of the cross-sectional form (as shown in FIG. 10).

Figure 11:
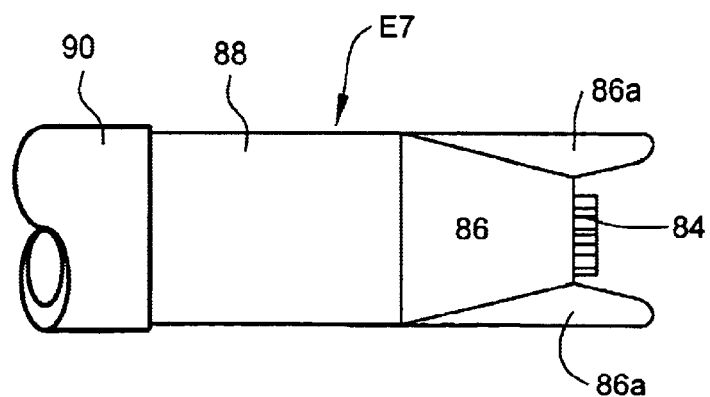
FIG. 11 is a diagrammatic side elevation of a seventh form of electrode unit constructed in accordance with the invention.

FIG. 11 shows the electrode assembly of the seventh form of electrode unit E7. This electrode assembly includes a central, tissue treatment (active) electrode constituted by a plurality of filaments made of tungsten or an alloy of tungsten or platinum, a tapered ceramic insulation sleeve 86, a return electrode 88, and an outer insulating sleeve 90. The insulation sleeve 86 is formed with a pair of diametrically-opposed, forwardly-extending wings 86a which project beyond the active electrode 84. The filaments constituting the active electrode 86 extend only a short distance from the distal end of the insulation sleeve 86, thereby constituting a very short brush electrode. The electrode unit E7 has, therefore, a large return:active electrode ratio, so that this electrode unit is intended primarily for a tissue removal by vaporisation. The electrode unit E7 is particularly useful for electrosurgical operations on meniscal cartilage or any other elongate laminate structure which is to be treated from the side, as the wings 86a can be used to trap the cartilage against the active electrode 84. The configuration of the wings 86a also assists in preventing unnecessary exposure of the active electrode 84, which may otherwise damage adjacent structures when working in the confined spaces commonly encountered in endoscopic surgery.

Figure 12A:
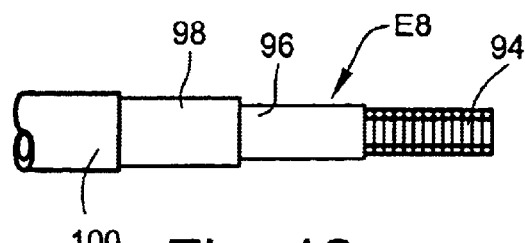
FIGS. 12a to 12d are diagrammatic side elevations of further forms of electrode unit constructed in accordance with the invention.
Figure 12B:
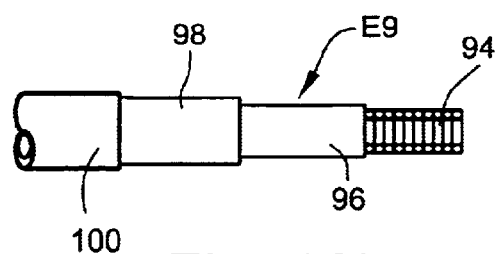
Figure 12C:
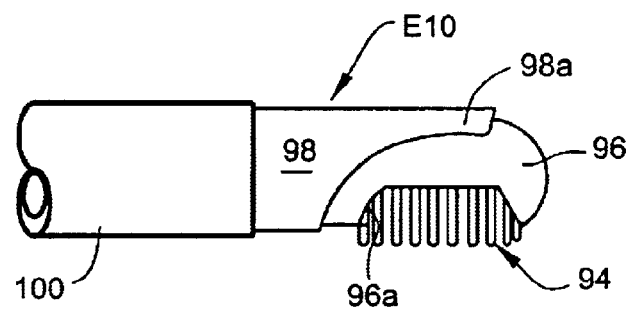
Figure 12D:
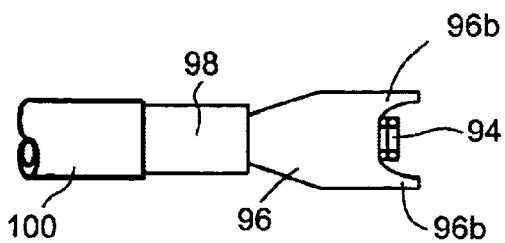

FIGS. 12a to 12d show eighth, ninth, tenth and eleventh forms of electrode unit E8 to E11, each of which incorporates an active electrode in the form of a coiled spring filament 94. The electrode units E8 to E11 each includes an insulation sleeve 96, a return electrode 98 and an insulating sheath 100. The electrode unit E8 of FIG. 12a is similar to that of FIG. 6a, being intended primarily for desiccation; and the electrode unit E9 of FIG. 12b is similar to that of FIG. 2, being intended primarily for vaporisation. The electrode unit E10 of FIG. 12c is similar to that of FIGS. 9 and 10, in that the coil electrode 94 is formed in a cut-out 96a formed in the side of the insulation sleeve 96, and the return electrode 98 is formed with a hood-like extension 98a which extends over the surface of the sleeve 96 which is opposite to the cut-out 96a. The electrode unit E10 can, thus, provide maximum tissue engagement for shallow working angle applications, and is another form of side-effect electrode. The electrode unit E11 of FIG. 12d is similar to that of FIG. 11, in that the insulation sleeve 96 is formed with a pair of diametrically-opposed, forwardly-extending wings 96b. In each of these embodiments, the active electrode 94 is made of an alloy of platinum.

The electrode units E8 to E11 are similar to the brush-type electrodes of FIGS. 2 to 11, and have similar surgical effects, apart from the fact that they eliminate the risk of splaying (which is advantageous in certain electro-surgical procedures). They have, however, the advantage of simplifying the assembly procedure, particularly when using platinum alloy materials.

It will be apparent that modification could be made to the electrosurgical instruments described above. For example, the insulation sleeves 16, 36, 46, 56, 66, 76, 86 and 96 could be made of a silicone rubber (such as a silicone polyurethene), glass, a polyimide or a thermoplastics material.

Figure 13:
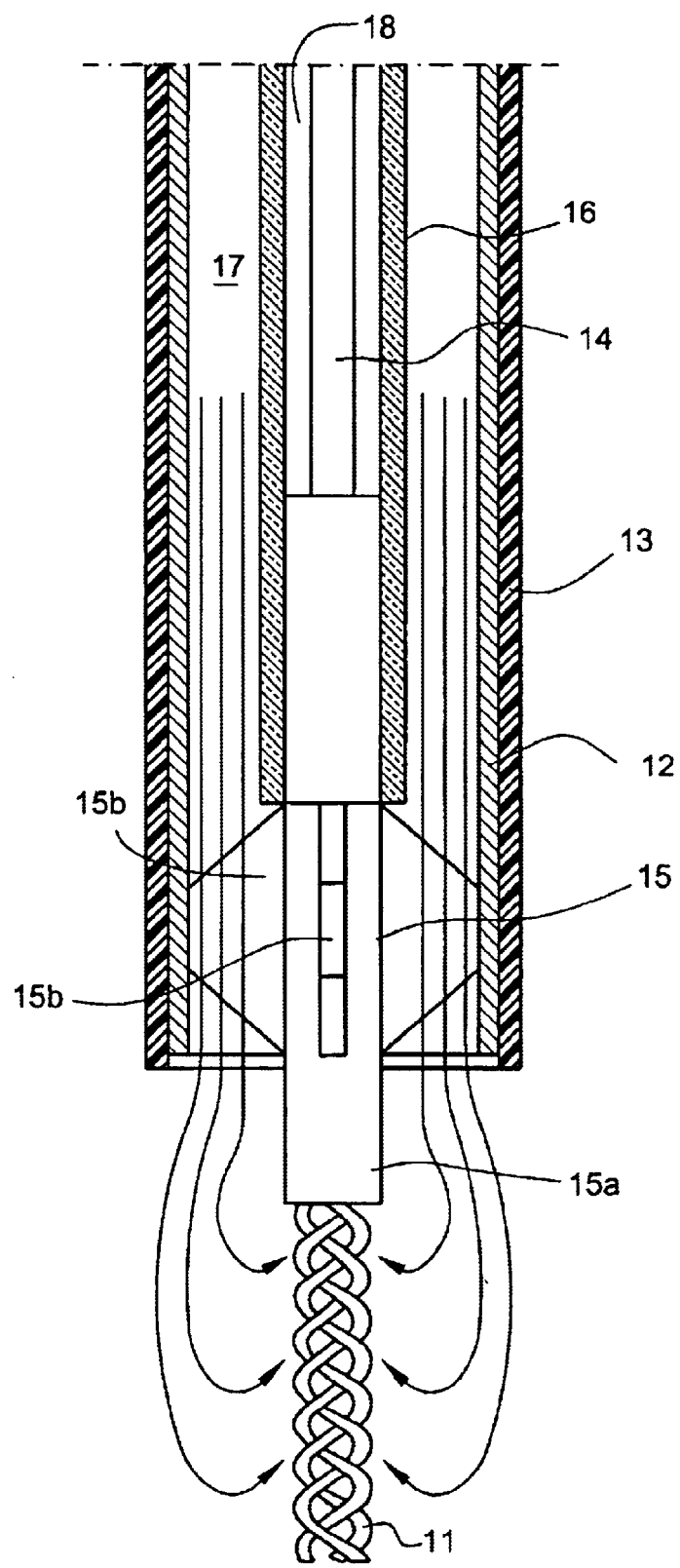
FIG. 13 is a schematic longitudinal sectional view of the distal end of a further form of electrosurgical instrument for use with the apparatus of FIG. 1.
Figure 14:
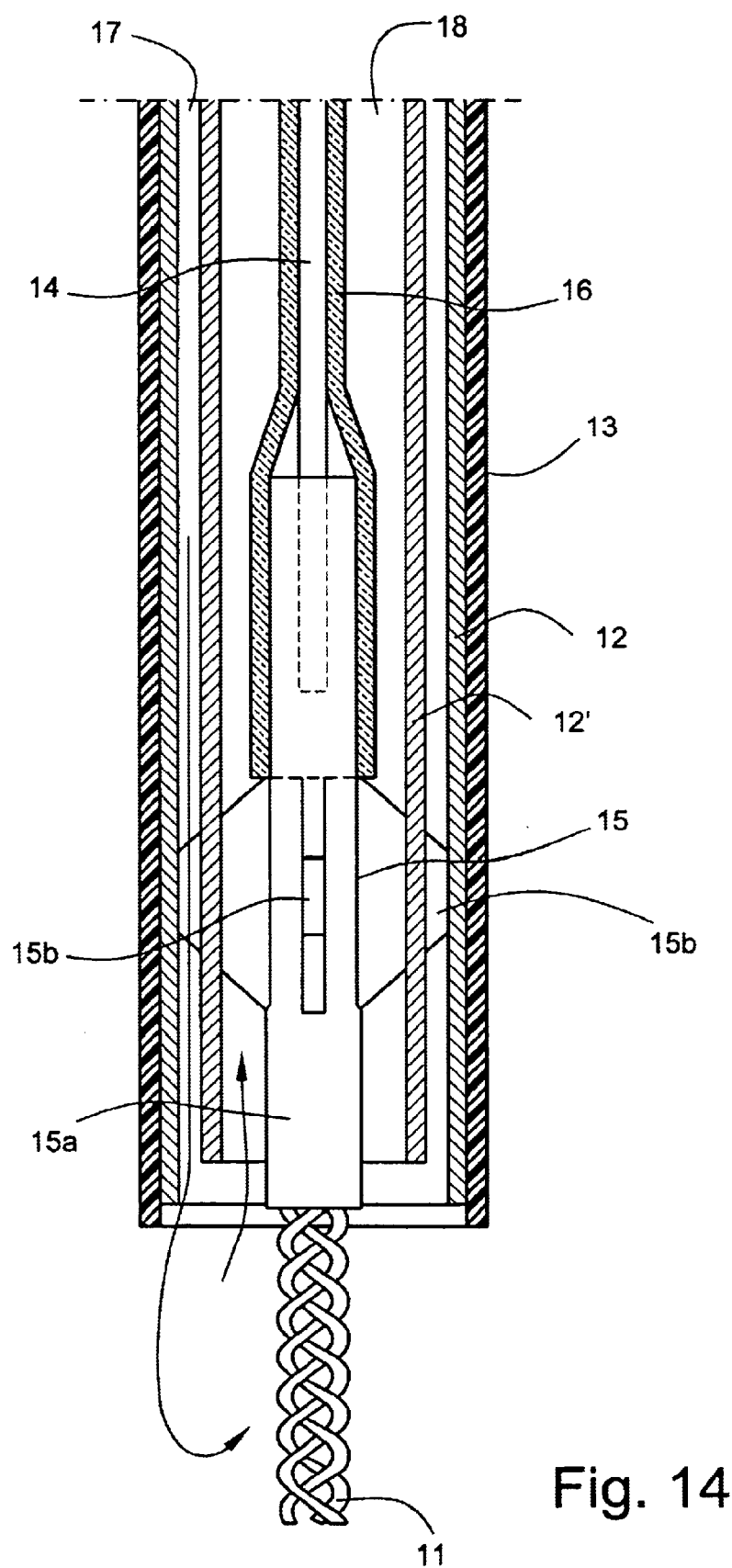
FIG. 14 is a schematic longitudinal sectional view of a second form of electrosurgical instrument for use with the apparatus of FIG. 1.

Referring now to FIGS. 13 and 14, an irrigated bipolar electrosurgical instrument that can be used in open air or gas filled environments will now be described.

FIG. 13 shows the distal end of the first form of irrigated electrosurgical instrument E12. The instrument E12 is formed with an electrode assembly at the distal end thereto, the electrode assembly comprising a central tissue treatment (active) electrode 11 and a tubular return electrode 12. The active electrode 11 is made of twisted noble metal (such as platinum/iridium or platinum/tungsten), and the return electrode is a stainless steel tube. The return electrode 12 is completely enveloped by a polyimide insulating sheath 13. The return electrode 12 extends the entire length of the electrosurgical instrument E12, and constitutes the shaft of the instrument.

The electrodes 11 and 12 are provided with current from the radio frequency (RF) generator 1 (not shown in FIG. 2), the return electrode 12 being directly connected to the generator and the active electrode 11 being connected via a copper conductor 14.

The generator 1 may be as described in the specification of our European Patent Application No.0754437. The active electrode 11 is held centrally within the return electrode 12 by means of a ceramic insulator/spacer 15. The insulator/spacer 15 has a generally cylindrical portion 15a surrounding the junction between the active electrode 11 and the conductor 14 and the adjacent regions of these two members, and four radially-extending, equispaced wings 15b which contact the internal circumferential wall of the return electrode 12 to hold the insulator/spacer, and hence the active electrode 11, centrally within the return electrode.

A tube 16, made of an insulating material such as PTFE, is a friction fit around the proximal end of the cylindrical portion 15a of the insulator/spacer 15, and extends substantially along the entire length of the instrument. The tube 16 defines, together with the return electrode 12, a coaxial saline supply channel 17, the interior of the tube 16 defining a saline return channel 18. In use, saline is fed to the channel 17 under gravity (no pumping being required), and saline is removed via the channel 18 and apertures (not shown) in the cylindrical portion 15a of the insulator/spacer 15 by means of suction. Preferably, the suction is carried out by a low noise pump (not shown) such as a moving vane pump or a diaphragm pump, rather than by using a high speed impeller. As the tubing leading to the pump will intermittently contain small quantities of saline, a large vacuum (at least 500 mBar) is required. However, the quantity of gas and liquid to be removed is comparatively small, and this permits the use of a moving vane or diaphragm pump, although a high volume peristaltic pump could also be used.

To circumvent the requirement for pump sterilisation, the pump operates via a disposable fluid trap (not shown) incorporating a 10 $\mu$m PTFE filter. This filter prevents both exhausted fluids and gas particulates from being drawn in by the pump and contaminating its workings and the surrounding environment.

The instrument E12 described above is intended for use in open air or gas filled environments, in body fluids, or by insertion into tissue by the creation of a conductive fluid environment around the tip of the instrument; and it is so arranged that it is possible to create a local saline field at a distal end of the instrument. This instrument E12 can, therefore, be used for laparoscopic applications. In use, saline is fed to the active electrode 11 via the channel 17, the saline providing a conductive medium to act as a conductive path between the tissue being treated and the return electrode 12. By varying the output of the generator 1, the instrument can be used for tissue removal by vaporisation, for cutting or for desiccation. In each case, as saline contacts the active electrode 11, it heats up until it reaches an equilibrium temperature dependent upon the power output of the generator 1 and the flow rate of the saline. In equilibrium, as fresh saline is fed via the channel 17 to the active electrode 11, the exterior temperature of the shaft is maintained at the same temperature as of that of the surrounding saline. As the insulating sheath 13 completely covers the external surface of the return electrode. 12, accidental contact between the return electrode and tissue is avoided.

One of the advantages of using a low saline flow rate, is that the saline temperature can reach boiling point. However, as there is a continuous flow of saline, there is a temperature gradient rise in the saline from the return electrode 12 to the active electrode 11. This temperature gradient is important, as the hotter saline adjacent to the active electrode 11 reduces the power threshold requirement to reach vaporisation. Although the flow rate requirement can be calculated on the basis of the input power, the flexibility of the generator 1 in maintaining optimum power density means that the flow rate is non-critical. For example, if the generator is set for 100 W, then the maximum flow rate is theoretically calculated as follows:

$$\text{Flow rate} = \text{power/specific heat capacity} -$$
$$100/4.2 \times 75 \text{ cc/s} -$$
$$0.32 \text{ cc/s} -$$
$$19 \text{ cc/min}$$

This assumes an initial saline temperature of 250° C., and a heat capacity of 4200 J/kg° C.

Although during vaporisation saline is brought into the vapour state, the vapour is only stable around the active electrode 11. Thus, the energy absorbed by virtue of the latent heat of vaporisation can be ignored, as this energy is recovered by freshly-arriving saline.

Another important factor is that, due to the very short circuit path of the saline, the current may be regarded as flowing along a number of different paths, which, therefore, do not have the same power density. Consequently, vaporisation can occur at flow rates higher than the calculated maximum, due to the unequal power densities within the saline environment. However, the amount of vaporisation occurring along the length of the active electrode 11 will depend upon the flow rate. As the saline is heated up by the active electrode 11, it is potentially damaging to tissue as it can cause thermal necrosis. It is important, therefore, that all the heated saline is recovered and exhausted from the patient before coming into contact with the tissue adjacent to the application site. It is for this reason that there is suction from the active electrode 11 to an exhaust reservoir (not shown). However, by ensuring that the suction occurs in excess, no saline can then escape from region of the active electrode 11 other than via the saline return channel 18. Any saline which escapes transversely beyond the exterior shaft falls away from the current path, and so is not heated. The priority is, therefore, to ensure that the hottest saline is removed. As the thermal gradient is at a maximum adjacent to the active electrode 11 this is the most appropriate exhaust point for the saline. It is for this reason that the saline is exhausted through the cylindrical portion 15a of the insulator/spacer 15.

Another important consideration in deciding the point of saline evacuation is the potential for blockage of the exhaust path. This could occur when cutting or vaporising tissue in such a way as to free small tissue particles which could easily block the exhaust. The exhaust point is, therefore, selected to be at the highest energy density point on the active electrode 11. This measure ensures that any tissue approaching the exhaust point is instantly vaporised into solution, thereby avoiding the potential for blockage.

Another significant advantage of ensuring a high degree of suction during tissue removal by vaporisation, is that any smoke which has not been absorbed by the saline is also evacuated. This is important, because smoke is capable of transmitting viable biological particles, and this could lead to infection.

As mentioned above, the power threshold for vaporisation is not well defined. If the instrument E12 were operating in a static conductive medium, then the vaporisation threshold would be well defined by an impedance switching point where the electrode impedance suddenly rises as a result of vapour pockets forming around the active electrode 11. The threshold is normally dependent upon the dissipation mechanism of the saline. In a static environment, the dissipation mechanism is predominantly by convection currents within the saline. Under these circumstances, the power threshold for vaporisation is defined by the input power into the electrode active region being in excess of the dissipation from the saline. However, in the embodiment, described above, the saline around the active electrode 11 is continually refreshed. If it were not, then the only dissipation mechanism would be by latent heat of vaporisation, and the saline would quickly evaporate. By providing a flow, the threshold power level is increased. However, the threshold power level is dependent on the saline refresh rate at the very periphery of the active electrode 11. The refresh rate at this boundary layer can be modified by altering the surface finish of the active electrode 11. For example, if the active electrode 11 had a smooth surface, then saline would be rapidly refreshed, as a rapid flow rate would be established. However, as the active electrode 11 has an irregular finish, the refresh rate of pockets within the irregular surface is diminished. Thus, the irregular surface traps saline (or at least delays the refresh), and so absorbs more power before being replaced. In other words, the power threshold is decreased by the irregular active electrode surface. This is a highly desirable property, as the electrode power requirement drops substantially without adversely effecting tissue performance. The threshold power is further reduced because the active electrode is constructed so as to provide a capillary action. Thus, even in the vaporised state, the active electrode 11 is intermittently wetted. By ensuring that this wetting wets the entire active electrode 11 by capillary action, there is a continual source of vapour which minimises the intermittent wetting, and so further reduces the power demand.

To vaporise tissue, it is necessary for the saline being fed from the channel 17 to be in contact with the tissue, as well as with the active electrode 11. The saline, therefore, has to form a constant drip enveloping the active electrode 11. The tip of the active electrode 11 is, therefore, designed so that the saline and the active electrode simultaneously contact tissue regardless of angle. If the flow of saline from the channel 17 to the active electrode 11 were completely annular, saline could flow from one side to the other, in which case the active electrode could be only partially enveloped. It is to prevent this, that the annular channel 17 is segmented by the wings 15b so as to ensure a saline flow on the uppermost surface. This also improves the adherence of the incoming saline by increasing the capillary action.

When the tip of the active electrode 11 comes into contact with the tissue, the region touching the tissue suddenly loses its ability to dissipate power via the saline. Whilst the return path is made up of a flow of saline, the tissue has no mechanism for power dissipation and therefore quickly heats up to the point where it is vaporised.

The effectiveness of the instrument in vaporising tissue is dependent on the ratio between the supported 'drip' and the length of the active electrode 11. A longer active electrode 11 is the most demanding, as the ability to maintain a constant 'drip' is reduced. However, once the active electrode 11 has vaporised a pocket within the tissue, so that the return electrode 12 is closer to the tissue surface, vaporisation becomes easier, as there is a smaller voltage drop across the saline, simply because it forms a smaller part of the electrical circuit.

By varying the output of the generator 1, the instrument E12 can also be used for desiccation (coagulation). In this case, the generator is controlled so that small vapour bubbles form on the surface of the active electrode 11, but insufficient vapour is produced to provide a vapour bubble (pocket) surrounding the active tip of the electrode 1, the vapour bubble being essential for tissue removal by vaporisation.

The generator 1 is controlled in such a manner that it has respective output ranges for tissue desiccation and for tissue removal by vaporisation. The former range is from 15 volts to 200 volts, and the latter range being peak voltages. In the vaporisation mode, the generator 1 is controlled in such a manner as to prevent the active electrode 11 overheating. This requires a reduction in the output voltage of the generator 1 once a vapour pocket has been established. The generator 1 and its control means are described in greater detail in the specification of our European Patent Application No. 0754437.

The coagulation from this electrode is vastly superior to any conventional bipolar electrode. The reasons are two fold. Firstly, the coagulation mechanism is not merely by electrical current in the tissue, but is also due to the heated saline. Secondly, under normal circumstances, the weakest link in providing electrical power to the tissue is the electrode/tissue interface, as this is the point of highest power density, and so imposes a power limit. If too high a power level is attempted, the tissue at the interface quickly desiccates, far faster than the larger cross-section of tissue forming the remaining circuit. If a lower power is selected, the interface can dissipate the temperature rise by mechanisms other than evaporation. Consequently, the interface remains intact longer, and so a greater depth of effect can be achieved. In this embodiment, the electrical interface is much stronger by virtue of the saline, and it is not possible completely to desiccate the target tissue. Thus, power can be delivered at a higher rate and for a longer period, resulting in a depth of effect which is purely time and power related.

FIG. 14 shows the distal end of the second form of electrosurhical instrument. This instrument is a modification of that shown in FIG. 2, 50 like reference numerals will be used for like parts, and only the modifications will be described in detail. The main modification is that the instrument of FIG. 2 includes two co-axial, tubular return electrodes 12 and 12', the return electrode 12' being slightly shorter than the return electrode 12 and being positioned therewithin. The annular gap between the two return electrodes 12 and 12' constitute the saline feed channel 17, and the saline return channel 18 is constituted by the annular gap between the return electrode 12' and the central construction constituted by the cylindrical portion 15a of the insulator/spacer 15 and the tube 16. The tube 16 is also modified to form a friction fit around both the proximal end of the cylindrical portion 15a of the insulator/spacer 15 and the active conductor 14.

The advantage of the instrument of FIG. 14 is that, when it is used to create vaporised pockets in a tissue surface (for example in an embedded tumour) there is less chance of the return path of saline to the saline return channel 18 being blocked. Thus, with the embodiment of FIG. 13 when a vapour pocket is created, some saline forming the conduction path between the active electrode 11 and the return electrode 12 can escape due to tissue obstructing the entrance to the return channel 18. This saline can be of a sufficiently high temperature to cause some peripheral tissue blanching. As tissue blanching is dependent upon the size of the instrument, the instrument of FIG. 13 should have small dimensions, so that the amount of peripheral blanching can be maintained at acceptable levels. With the embodiment of FIG. 14, on the other hand, the return path of saline from the active electrode 11 to the return channel 18 will then never be obstructed by tissue. Moreover, when the conduction path between the active electrode 11 and the return electrode 12 is obstructed, the portion of saline obstructed from the active electrode—1 has a reduced power dissipation. This reduced dissipation arises from the fact that both inlet and output saline are connected to the return channel 18, 50 the impedance is lower to the extent that the majority of power dissipation then occurs in the obstructing tissue.

The instrument of FIG. 14 is, therefore, less suitable for miniaturisation than that of FIG. 13, due both to the extra tubing (the extra return electrode 12') and the aspect ratio of the tip (i.e. the active electrode 11 cannot protrude as much per diameter due to the saline exhaust being stepped further back). This exhaust has to be positioned further back, as it is passed through the second return electrode 12'. If it were not so positioned, it would cause too great a power distribution over the length of the active electrode 11.

The exhaust saline from the instrument of FIG. 14 may also contain tissue particulates. As the exhaust path does not necessarily pass through a vaporising region, this imposes a limit to the minimum size of this version of the instrument, due to the potential for blockage of the exhaust path.

The best vaporising performance for each of the instruments described above is when the active electrode 11 is designed to trap, or at least interrupt, saline flow. The reason for this is quite simple, namely that the longer saline can be kept in close proximity to the active electrode 11 the more power it absorbs, and hence the greater the propensity to form a vapour. Wire or hollow forms of active electrode are, therefore, the most effective. It would, for example, be possible to replace the twisted form of wire form of active electrode by an active electrode in the form of a coil. It would also be possible to improve vaporisation by partially obscuring the active electrode/saline interface by masking with sprayed ceramic, sprayed ceramic being deposited at a particulate non-uniform coating.

The instruments described above in connection with FIGS. 13 and 14 have a number of advantages namely:
1. Each can provide a monopolar like action with only one electrode (the active electrode 11) in direct tissue contact;
2. Each provides immediate tissue debulking (vaporisation) in a manner similar to that obtained with laser instruments;
3. RF current is confined to the area of treatment, thereby reducing collateral or deep thermal effects, and eliminating remote burns;
4. There is minimal smoke when cutting or vaporising, due to the cooling, condensing and dissolving effects of the surrounding saline. Any smoke produced is rapidly removed due to the suction adjacent to the active electrode 11;
5. As the current path within the electrode assembly is bi-directional, there is minimal capacitive coupling at any electrode entry points;
6. The saline provides an excellent active electrode/tissue interface which preserves current flow for a controlled depth of coagulation, this being dependent purely on power and application time.
7. The saline connection prevents high impedance conditions which could cause significant carbonization which is known to be detrimental to tissue healing, and increases the risk of adhesion formation;
8. The excellent low impedance active electrode/tissue interface permits the use of much higher powers for rapid effects. This is particularly useful for quick non-carbonizing coagulation; and
9. Much higher power levels are supported than for conventional bipolar electrosurgery. In practice, conventional bipolar electrosurgery is only effective to a limit of 40 W or 50 W, as higher power levels result in overheating and carbonization. With the electrode configuration of FIGS. 13 and 14 power levels in excess of 200 W can be supported.

It will be apparent that modifications could be made to the instruments described above in connection with FIGS. 13 and 14. Thus, the active electrode 11 could be of any other suitable form, such as a needle electrode or a hollow, perforated part-spherical electrode made, for example, of platinum/iridium, and the insulator/spacer 15 would be made of silicone rubber or glass. It would also be possible to replace saline as the conductive medium with a conductive gas such as argon. In this case, the argon would need to be pumped to the region of the active electrode 11 through the channel 17, and there would be no need to remove the argon via the return channel 18, there being no danger of collateral tissue damage from hot argon. In this case also, a modified form of RF generator would be needed. The entire electrode assembly could be constructed as a flexible or rigid assembly, and could also incorporate means for steering or manipulating the active tip, or insertion into tissue.

What is claimed is:

1. A method of corrective treatment of bladder neck descent including the steps of:
    obtaining access via a conduit to a cavity in a region of a treatment site which includes the bladder neck;
    introducing an electrosurgical instrument into the cavity via the conduit;
    supplying electrically conductive fluid to the treatment site;
    using the instrument to apply radio frequency power to the treatment site via first and
    second electrodes on the instrument, wherein a conductive path between the first and second electrodes is completed by means of the conductive fluid, and inducing, as a result of applied radio frequency power, shrinkage of the pelvic floor thereby to correct the bladder neck descent.

2. A method according to claim 1 wherein the conduit is a natural conduit in the body of the patient.

3. A method according to claim 1 wherein the conduit is provided by a cannula, and the method further comprises the step of creating an artificial conduit to provide access to the cavity by means of a cannula.

4. A method according to claim 1 wherein the cavity is opened by distending the cavity using the conductive fluid.

5. A method according to claim 1 wherein the cavity is opened naturally by means of anatomical structures.

6. A method according to claim 1 wherein the method further comprises the step of using indirect visualization means to view the site.

7. A method of corrective treatment for bladder neck descent using an electrosurgical instrument having a pair of electrodes, the method comprising the steps of:
    introducing the instrument into a cavity adjacent a treatment site which includes the bladder neck;
    irrigating the treatment site with an electrically conductive liquid;

applying radio frequency power to the electrodes of the instrument, and completing a conductive pathway between the electrodes of the instrument by means of the conductive fluid;

heating the liquid by virtue of current passing through the liquid between the electrodes, but controlling power dissipated into the conductive liquid to prevent the formation of a vapour pocket in the region of at least one of the electrodes; and thermally inducing shrinkage of the pelvic floor to correct for bladder neck descent.

8. A method according to claim 7 further comprising the step of manipulating the instrument to bring at least one of the electrodes adjacent the pelvic floor, and wherein thermal shrinkage of the pelvic floor occurs at least in part as a result of radio frequency current passing between the electrodes via tissue at the treatment site, resulting in the heating of tissue.

9. A method according to claim 8 wherein thermal shrinkage of the pelvic floor occurs additionally as a result of heat from the conductive fluid.

10. A method according to claim 7 wherein the instrument is introduced into the cavity via a natural body conduit.

11. A method according to claim 7 wherein the instrument is introduced into the cavity via a cannula.

12. A method according to claim 7 further comprising the step of distending the cavity by means of the electrically conductive liquid.

13. A method of correcting bladder neck descent, the method comprising the steps of:

obtaining access to a cavity adjacent a treatment site which includes the bladder neck, and introducing an electrosurgical instrument having a pair of electrodes into the cavity;

irrigating the treatment site with an electrically conductive fluid, and completing a conduction path between the electrodes by means of the electrically conductive fluid;

applying radio frequency power to the treatment site by applying an oscillating radio frequency voltage across the electrodes, thermally to induce shrinkage of the pelvic floor and thereby correct bladder neck descent.

* * * * *